US010221363B2

(12) United States Patent
Schabron et al.

(10) Patent No.: US 10,221,363 B2
(45) Date of Patent: *Mar. 5, 2019

(54) METHODS OF SUCCESSIVE ELUTION OF COMPONENTS OF HYDROCARBONS

(71) Applicant: The University of Wyoming Research Corporation, Laramie, WY (US)

(72) Inventors: John F. Schabron, Laramie, WY (US); Ryan B. Boysen, Laramie, WY (US); Eric W. Kalberer, Laramie, WY (US); Joseph F. Rovani, Jr., Laramie, WY (US)

(73) Assignee: The University of Wyoming Research Corporation, Laramie, WY (US)

( * ) Notice: Subject to any disclaimer, the term of this patent is extended or adjusted under 35 U.S.C. 154(b) by 51 days.

This patent is subject to a terminal disclaimer.

(21) Appl. No.: 15/167,766

(22) Filed: May 27, 2016

(65) Prior Publication Data

US 2016/0272899 A1    Sep. 22, 2016

Related U.S. Application Data

(63) Continuation of application No. 13/237,568, filed on Sep. 20, 2011, now Pat. No. 9,353,317.

(51) Int. Cl.
| | | |
|---|---|---|
| *C10G 53/08* | (2006.01) | |
| *C10G 25/00* | (2006.01) | |
| *B01D 15/26* | (2006.01) | |
| *C10G 25/12* | (2006.01) | |
| *G01N 30/46* | (2006.01) | |
| *G01N 33/28* | (2006.01) | |
| *B01J 20/281* | (2006.01) | |
| *B01J 20/283* | (2006.01) | |
| *B01J 20/284* | (2006.01) | |
| *B01J 20/286* | (2006.01) | |
| *B01J 20/287* | (2006.01) | |
| *B01D 15/00* | (2006.01) | |
| *G01N 30/14* | (2006.01) | |
| *G01N 30/08* | (2006.01) | |
| *G01N 30/88* | (2006.01) | |
| *G01N 30/02* | (2006.01) | |

(52) U.S. Cl.
CPC ........... *C10G 25/003* (2013.01); *B01D 15/00* (2013.01); *B01D 15/265* (2013.01); *B01J 20/281* (2013.01); *B01J 20/283* (2013.01); *B01J 20/284* (2013.01); *B01J 20/286* (2013.01); *B01J 20/287* (2013.01); *C10G 25/12* (2013.01); *C10G 53/08* (2013.01); *G01N 30/14* (2013.01); *G01N 30/461* (2013.01); *G01N 30/468* (2013.01); *G01N 33/2823* (2013.01); *C10G 2400/30* (2013.01); *G01N 33/2835* (2013.01); *G01N 2030/027* (2013.01); *G01N 2030/085* (2013.01); *G01N 2030/143* (2013.01); *G01N 2030/8854* (2013.01)

(58) Field of Classification Search
CPC ...... B01J 20/281–20/287; B01D 15/08; B01D 15/265; B01D 15/424; B01D 15/426; G01N 2030/027; G01N 30/461; G01N 30/468; C10G 25/003; C10G 25/12; C10G 53/08
See application file for complete search history.

(56) References Cited

U.S. PATENT DOCUMENTS

| | | | |
|---|---|---|---|
| 4,493,765 A | 1/1985 | Long et al. | |
| 4,628,204 A | 12/1986 | Maes | |
| 4,634,680 A | 1/1987 | Kingsley | |
| 4,865,741 A | 9/1989 | Nolte et al. | |
| 4,988,446 A | 1/1991 | Haberman et al. | |
| 4,990,773 A | 2/1991 | Supernaw et al. | |
| 5,092,983 A | 3/1992 | Eppig et al. | |
| 5,574,215 A | 11/1996 | Bunger et al. | |
| 5,861,228 A | 1/1999 | Descales et al. | |
| 5,969,237 A | 10/1999 | Jones et al. | |
| 6,773,921 B1 | 8/2004 | Schabron et al. | |
| 7,875,464 B2 | 1/2011 | Schabron et al. | |
| 8,241,920 B2 | 8/2012 | Schabron et al. | |
| 8,273,581 B2 | 9/2012 | Scharon et al. | |
| 8,492,154 B1 | 7/2013 | Schabron et al. | |
| 8,530,240 B1 | 9/2013 | Schabron et al. | |
| 8,628,970 B1 | 1/2014 | Schabron et al. | |
| 9,353,317 B2 | 5/2016 | Schabron et al. | |

(Continued)

FOREIGN PATENT DOCUMENTS

| | | |
|---|---|---|
| EP | 400989 A | 5/1990 |
| WO | 0077120 A2 | 12/2000 |

(Continued)

OTHER PUBLICATIONS

U.S. Appl. No. 13/237,568, filed Sep. 20, 2011. First Named Inventor: John F. Schabron.

(Continued)

*Primary Examiner* — Renee Robinson
(74) *Attorney, Agent, or Firm* — Santangelo Law Offices, P.C.

(57) ABSTRACT

The inventive technology may involve, in particular embodiments, novel use of a non-porous, high surface energy stationary phase to adsorb, in reversible fashion, the most polar component of a resins fraction of an input hydrocarbon when a mobile phase is passed over the stationary phase. Such reversible adsorption prevents irreversibly adsorption of such components on active stationary phase(s) downflow of the non-porous, high surface energy stationary phase, thereby conserving stationary phase costs and increasing resolution of resins elutions, and accuracy of hydrocarbon component results. Aspects of the inventive technology may also involve a novel combination of a solubility based asphaltene component fractionating and analysis method and an adsorption chromatography method for separating and/or analyzing saturate, aromatics and resins components of an input hydrocarbon.

27 Claims, 10 Drawing Sheets

(56) References Cited

U.S. PATENT DOCUMENTS

| | | | |
|---|---|---|---|
| 2003/0211621 | A1 | 11/2003 | Rovani et al. |
| 2007/0048874 | A1 | 3/2007 | Schabron et al. |
| 2011/0062058 | A1 | 3/2011 | Rogel et al. |
| 2011/0066441 | A1 | 3/2011 | Orvalles et al. |
| 2011/0120950 | A1 | 5/2011 | Schabron et al. |
| 2012/0016168 | A1 | 1/2012 | Schabron et al. |
| 2012/0160015 | A1 | 6/2012 | Ovalles et al. |

FOREIGN PATENT DOCUMENTS

| | | |
|---|---|---|
| WO | 0077120 A3 | 12/2000 |
| WO | 02063292 A1 | 8/2002 |
| WO | 03096011 A1 | 11/2003 |
| WO | 2011032123 A2 | 3/2011 |
| WO | 2011032125 A2 | 3/2011 |
| WO | 2011113017 A2 | 9/2011 |
| WO | 2011/127044 | 2/2012 |

OTHER PUBLICATIONS

"Standard Test Method for Separation of Asphalt into Four Fractions1," ASTM International, Designation D4124-09.
"Energy and Environmental Profile of the US Petroleum Refining Industry," 1988, Prepared by Energetics Inc. for U.S. Department of Energy Office of Industrial Technologies.
Schabron, J.F., et al., "Asphaltene Determinator Method for Automated On-Column Precipitation and Redissolution of Pericondensed Aromatic Asphaltene Components," Energy Fuels 2010, 24, 5984-5996, DOI: 10.102/ef100822f.
Fan, T. et al., "Rapid and Accurate SARA Analysis of Medium Gravity Crude Oils," Energy & Fuels 2002, 16, 1571-1575.
Schabron, J.F. et al., "On-column precipitation and re-dissolution of asphaltenes in petroleum residua," Fuel 87 (2008) 165-176.
Grizzle, Patrick L, et al., "Automated Liquid Chromatographic Compound Class Grou-Type Separation of Crude Oils and Bitumens Using Chemically Bonded Aminosilane," Anal. Chem. 1986, 58, 2389-2396.
Jewell, D.M. et al., "Ion-Exchange, Coordination, and Adsorption Chromatographic Separation of Heavy-End Petroleum Distillates," Laramie Energy Research Center, Analytical Chemistry, vol. 44, No. 8, Jul. 1972, p. 1391.
Jiang, C et al., "TLC-FID (Iatroscan) analysis of heavy oil and tar sand samples," Organic Geochemistry 39 (2008) 1210-1214.
Karlsen, D.A. et al., "Analysis of petroleum fractions by TLC-FID: applications to petroleum reservoir description," Org. Geochem. vol. 17, No. 5, pp. 603-617, 1991.
Kharrat, A. et al., "Issues with Comparing SARA Methodologies," Energy & Fuels 2007, 21, 3618-3621.
Masson, J-F et al., "Dynamics of Bitumen Fractions by Thin-Layer Chromatography/Flame Ionization Detection," Energy & Fuels 2001, 15, 955-960.
Radke, M et al., "Preparative Hydrocarbon Group Type Determination by Automated Medium Pressure Liquid Chromatography," Anal. Chem. 1980, 52, 406-411.
Schabron, J.F. et al.; "Petroleum Processing Efficiency Improvement," Topical Report, May 2011.
Wiehe, Irwin A. et al.; "The Oil Compatibility Model and Crude Oil Incompatibility," Energy & Fuels 2000, 14, 56-59.
Fan, Z et al.; "Challenges in Processing Bitumens and Heavy Oils," Prepr. Pap.-Am. Chem. Soc., Div. Petr. Chem. 2009, 54 (1), 4.
"Canada regulator approves Enbridge diluent Line," Reuters, Business & Financial News, Feb. 19, 2008, Calgary, Alberta.
"Opportunity Crudes Report II: Technologies and Strategies for Meeting Evolving Market and Environmental Challenges," Hydrocarbon Publishing Company, an updated and expanded study of the 2006 report titled "Opportunity Crudes: Technical Challenges and Economic Benefits."
USPTO Office Action for U.S. Appl. No. 11/510,491 dated Dec. 9, 2010.
USPTO Office Action for U.S. Appl. No. 11/510,491 dated Sep. 3, 2010.
USPTO Office Action for U.S. Appl. No. 11/510,491 dated Jul. 13, 2009.
USPTO Office Action for U.S. Appl. No. 11/510,491 dated Mar. 30, 2010.
USPTO Office Action for U.S. Appl. No. 11/510,491 dated Mar. 2, 2011.
http://www.specialchem4adhesives.com/resources, Determining Critical Surface Tension of Solid Substrates, printed Sep. 13, 2011, 3 pages.
Energy Information Administration/Capacity Report 2001.
Robinson, P. R., Petroleum Processing Overview, Practical Advances in Petroleum Processing 2006:1-78.
Rogel, E. et al. Asphaltene Stability in Processed Samples using Solubility Profile Analysis, Prepr. Pap.-Am. Chem. Soc. Div. Pet. Chem. 2011, 56(1), 3.
Ovalles, C. et al. Characterization and Preparative Separation of Heavy Crude Oils, their fractions and thermally Cracked Products by the Asphaltene solubility Fractions Method, Prepr. Pap.-Am. Chem. Soc. Div. Pet. Chem. 2011, 56(1), 8.
Schabron J. F. et al., Total Pericondensed Aromatic (TPA) Determination as an Alternative to Gravimetric Asphaltenes, Prepr. Pap.-Am. Chem. Soc. Div. Pet. Chem. 20011, 56(1), 38.
Rogel, E. et al. Determination of Asphaltenes in Crude Oil and Petroleum Products by the on Column Precipitation Method, Energy Fuels 2009, 23, 4515-4521.
Ovalles, C. et al. Characterization of Heavy Crude Oils, Their Fractions, and Hydrovisbroken Products by the Asphaltene Solubility Fraction Method, dx.doi.org/10.1021/ef201499f | Energy Fuels 2012, 26, 549-556, Published: Dec. 7, 2011.
Lopez-Linares, F. et al. Adsorption of Athabasca Vacuum Residues and Their Visbroken Products over Macroporous Solids: Influence of Their Molecular Characteristics, dx.doi.org/10.1021/ef201047z | Energy Fuels 2011, 25, 4049-4054, Published Aug. 17, 2011.
Rogel, E., Asphaltene Chemical Characterization as a Function of Solubility: Effects on Stability and Aggregation, dx.doi.org/10.1021/ef2013979 | Energy Fuels, Published Nov. 7, 2011.
Schabron, J. F. et al. The Waxphaltene Determinator Method for Automated Precipitation and Re-Dissolution of Wax and Asphaltene Components, Energy Fuels, Article ASAP, DOI: 10.1021/ef300184s, Feb. 27, 2012.
Parallel U.S. Appl. No. 12/970,535, Office action dated Mar. 2, 2011.
Parallel U.S. Appl. No. 12/970,535, Office action dated Oct. 7, 2011.
Parallel U.S. Appl. No. 12/970,535, Office action dated Jan. 12, 2012.
Parallel U.S. Appl. No. 13/243,782, Office action dated Mar. 23, 2012.
Parallel U.S. Appl. No. 12/970,535, Notice of Allowance dated Jun. 8, 2012.
Parallel U.S. Appl. No. 13/243,782, Office action dated Jun. 27, 2012.
Parallel U.S. Appl. No. 13/243,782, Notice of Allowance dated Aug. 3, 2012. 9 pages.
Schabron, J. F. et al., Asphaltene Determinator Method for Automated On-Column Precipitation and Redissolution of Pericondensed Aromatic Asphaltene Components. Energy Fuels 2010, 24, 5984-5996.
Standard Test Method for Separation of Asphalt into Four Fractions. Designation: D4124-09. 383-390.
"Energy and Environmental Profile of the US Petroleum Refining Industry," 1988, Prepared by Energetics Inc. for U.S. Department of Energy Office of Industrial Technologies. 124 pages.
"Standard Test Method for Molecular Weight (Relative Molecular Mass) of Hydrocarbons by Thermoelectric Measurement of Vapor Pressure," ASTM Designation: D 2503-82 (Reapproved 1997), 871-873.
Andersen, S.I. et al., 1991, "Aggregation of Asphaltenes as Determined by Calorimetry," Journal of Colloid and Interface Science, 142, 497-502, 1991.
Barton, A.F., 1974, "Solubility Parameters," Chemical Reviews, 75 (6), 731-753.

(56) References Cited

OTHER PUBLICATIONS

Bodusynski, M.M. et al., 1982, Separation of Solvent-Refined Coal into Solvent-Derived Fractions, Analytical Chemistry, 54, 372-375.
Burrell, H., 1955, Solubility Parameters. Interchemical Review, 3-16, 32-46.
Carrier, H. et al; Acoustic method for measuring asphaltene flocculation in crude oil, Journal of Petroleum Science and Engineering, pp. 111-117.
Cartz, L., ch. 3, Ultrasonic Testing, Nondestructive Testing, 1995, pp. 81-98.
Del Bianco, A. et al., 1993, Thermal Cracking of Petroleum Residues 1. Kinetic Analysis of the Reaction. Fuel, 72 (1). 81-85.
Heithaus, J.J., 1962, Measurement and Significance of Asphaltene Peptization, Journal of the Institute of Petroleum 48 (458), 45-53.
Hildebrand, J.H. et al., 1970, Regular and Related Solutions, Van Nostrand Reinhold, NY, pp. 24-27, pp. 152-153, pp. 212-215.
Jones et al. Development of an ultrasonic oil stability monitor for the assessment of asphaltene aggregation in hydrocarbon streams, Proceed. Intern. Conf. Mitigat. Heat Exch. Foul. Econ. Envir. Implic. Banff, AB, Canada, Jul. 1999, 84-94.
Long, R.B. et al., 1989, Studies in Petroleum Composition, Revue de Institute Francais du Petrole, abstract.
Long, R.B., 1979, Chemistry of Asphaltenes. Preprints, Div. Petroleum Chemistry, American Chemical Society, 24, 891-901.
Magaril, R.Z. et al., 1968, Study of the Mechanism of Coke Formation in the Cracking of Petroleum Resins, International Chemical Engineering 8 (4), 727.
McClements, D.J., Ultrasonic Measurements in Particle Size Analysis, University of Massachusetts, Amherst, USA, Encyclopedia of Analytical Chemistry (Applications, Theory and Instrumentation) pp. 1-8.
Pal R. et al., 1989, Viscosity/Concentration Relationships for Emulsions. Journal of Rheology, 33 (7), 1021-1045.
Pauli, A.T. 1996, Asphalt Compatibility Testing Using the Automated Heithaus Titration Test, Preprints, Division of Fuel Chemistry, American Chemical Society, 41 (4), 1276-1281.
Pauli, A.T. et al., 1998, Relationships Between Asphaltenes, Heithaus Compatibility Parameters, and Asphalt Viscosity. Petrol. Science and Technology, 16 (9&10), 1125-1147.
Pauli, A.T. et al., Stability and Compatibility Testing of Petroleum and Asphalt, American Laboratory, Sep. 2003, 2 pages.
Phillips, C.R, et al. 1985, Kinetic Models for the Thermal Cracking of Athabaska Bitumen, Fuel 64(5), 678-691.
Scatchard, G. 1931, Equilibria in Non-Electrolyte Solutions in Relation to the Vapor Pressure and Densities of the Components, Chemical Reviews, 321-333.
Schabron, J.F. et al. Coking indexes using the Heithaus titration and asphaltene solubilitl, Preprints American Chemical Society, Division of Petroleum Chemistry (1999), 44(2), 187-189.
Schabron, J.F. et al., 1998, The Solubility and Three-Dimensional Structure of Asphaltenes. Petroleum Science and Technology, 16 (3-4), 361-376.
Schabron, J.F. et al., 1999 Petroleum Residua Solubility Polarity Map: Stability Studies of Residua Pyrolysis, Department of Energy Report under contract # DE-FC26-98FT40322 Task, 1.2, 24 pages.
Schabron, J.F. et al., 2000 Deposition from Heavy Oils. Department of Energy Report under contract # DE-FC26-98F140322, 35 pages.
Schabron, J.F. et al., 2001b, Molecular Weight Polarity Map for Residua Pyrolysis, Fuel, 80 (4), 529-537.
Schabron, J.F. et al., 2001c, Non-Pyrolytic Heat Induced Deposition from Heavy Oils, Fuel, 80 (7) 919-928.
Schabron, J.F., et al., 2002b, Residua Coke Formation Predictability Maps, Fuel, 81 (17) 2227-2240.
Schabron, J.F. et al., 2001a, Predicting Coke Formation Tendencies, Fuel, 80 (10) 1435-1446.
Schabron, J.F. et al., 2002, Characterization of Residua During Pyrolysis, Preprints, Div. of Petroleum Chemistry, American Chemical Society, 47 (1), 17-21.
Schabron, J.F. et al., 1993, The Characterization of Petroleum Residua. U.S. Dept of Energy Report under contract # DE-FC21-86MC11076I, 68 pages.
Schabron, J.F. et al., 2002, Thermal Analysis for Monitoring Incipient Coke Formatio, US Department of Energy Report DE/FG36/01G011018, 18 pages.
Schabron, J.F. et al , 2002, Coke Formation Process Model for Petroleum Refining Efficiency Improvemen, US Department of Energy Report under contract # DE/FG36/01G011018, 40 pages.
Schabron, J.F. et al., 2004, Refinery Efficiency Improvement Ultrasonic Spectroscopy and WRI Coking Indexes, WRI Report 04-R009 to DOE under Cooperative Agreement DE-FC26-98FT40322. 46 pages.
Singh, I.D., V. Kothiyal, V. Ramaswamy, and R. Krishna, 1990, Characteristic Changes of Asphaltenes During Visbreaking of North Gujarat Short Residue. Fuel, 69 (3), 289-292.
Small, P.A., 1953, Some Factors Affecting the Solubility of Polymers, Journal of Applied Chemistry, 71-80.
Snyder, L.R., 1968, Principles of Adsorption Chromatography. Marcel Dekker, Inc., New York, 206-210.
U.S. Appl. No. 60/711,599, filed Aug. 25, 2005.
Wiehe, I.A., 1993, A Phase-Separation Kinetic Model for Coke Formation, Ind. Eng. Chem. Res., 32 (11), 244x 2454.
Wiehe, I.A., 1996, Two-Dimensional Solubility Parameter Mapping of Heavy Oils, Fuel Science and Technology International, 14 (1&2), 289-312.
Bodusynski, M.S. et al., 1987, "Composition of heavy petroleums: 1. molecular weight, hydrogen deficiency, and heteroatom concentration as a function of atmospheric equivalent boiling point up to 1400 degrees F" Energy & Fuels, 1, 2-11.
Schabron, J.F., et al., 2006, "Initial studies using ultrasonic spectroscopy for monitoring changes in residua with pyrolysis," Fuel 85, 2093-2105.
Chiantore, Oscar and Simonelli, Alessandra, "Precipitation-redissolution Liquid Chromatography of Styrene-ethyl Acrylate Copolymers," Polymer Engineering and Science, Aug. 1999, vol. 39 No. 8, p. 1383-1388.
Cortell, Jessica M. et al., "Infulence of Vine Vigor on Grape (*Vitis vinifera* L. Cv. Pino Noir) Anthrocyanins. 2. Anthocyanins and Pigmented Polymers in Wine," J. Agric. Food Chem. 2007, 55, p. 6585-6595.
Aske, Narve et al.; "Determination of Saturate, Aromatic, Resin, and Asphaltenic (SARA) Components in Crude Oils by Means of Infrared and Near-Infrared Spectroscopy," Energy & Fuels, 2001, 15, 1304-1312.
Corbett, L.W., "Composition of Asphalt Based on Generic Fractionation, Using Solvent Deasphaltening, Elution-Adsorption Chromatography, and Densimetric Characterization," Analytical Chemistry, p. 576-579.
McCarthy, James E. et al.; "EPA's Regulation of Coal-Fired Power: Is a "Train Wreck" Coming?", Congressional Research Service, CRS Report for Congress, Aug. 8, 2011, 7-5700, R41914. 50 pages.
"Standard Test Method for n-Heptane Insulbles1", Designation: D 3279-97 (Reapproved 2001).
E. Rogel et al., "Asphaltene Stability in Crude Oil and Petroleum Materials by Solubility Profile Analysis," Energy and Fuel, 24 (8), pp. 4369-4374 (2010) (Published on Web Jul. 28, 2010).
F.P. Burke et al., "Liquid Column Fractionation: A Method of Solvent Fractionation of Coal Liquefication and Petroleum Products," Fuel, vol. 58, pp. 539-541 (1979).
F.K. Schweighart et al., "Development of SRC-I Product Analysis. vol. 2. Evaluation of Analytical Techniques for SRC-I Characterization, Recycle Solvent Studies, and Product Fractionation Studies," published Sep. 1, 1983.
M.M. Boduszynski, "Composition of Heavy Petroleums. 1. Molecular Weight, Hydrogen Deficiency, and Heteroatom Concentration as a Function of Atmospheric Equivalent Boiling Point up to 1400 F (760 C)," Energy & Fuels, vol. 1, No. 1, pp. 2-11 (1987).
M.M. Boduszynski et al, "Separation of Solvent0Refined Coal into Solvent-Derived Fractions," Analyical Chemistry, vol. 54, pp. 372-375 (1982).

(56) References Cited

OTHER PUBLICATIONS

Parallel U.S. Appl. No. 13/243,782, Office action dated Jun. 27, 2012. 9 pages.
Ovalles, C. et al. Predicting Reactivity of Feedstocks to Hydroprocessing by Using Asphaltene Characterization Techniques. Prepr. Pap.-Am. Chem. Soc., Div. Energy Fuels Chem. 2012, 57(2), 763. 3 pages.
Rogel, E. et al. Sediment Formation in Residue Hydroconversion Processes and Its Correlation to Asphaltene Behavior. Prepr. Pap.-Am. Chem. Soc., Div. Energy Fuels Chem. 2012, 57(2), 745.
Schabron, J.F. Use of the Asphaltene Determinatorlm Method to Monitor Vacuum Residue Stability to Improve Refinery Distillation Efficiency, 2011.
Parallel U.S. Appl. No. 13/490,307; Office action dated Oct. 4, 2012. 10 pages.
McLean J. B. et al. Reactivity Screening of Feedstocks for Catgalytic Coal/Oil Co-Processing, Sep. 1986, http://web.anl.gov/PCS/acsfuel/preprint%20archive/Files/31_4_ANAHEIM_09-86_0169.pdf. 12 pages.
Mariaca-DomAnguez et al. "Reactivity of Fluid Catalytic Cracking Feedstocks as a Function of Reactive Hydrogen Content", Petroleum Science and Technology, 2004, vol. 22, Issue 1-2, pp 13-29.
Johnson and Moyse, "Pretreatment of resid FCC feedstocks", Jul. 2004, http://www.digitalrefining.com/article/1000161.
Parallel U.S. Appl. No. 12/970,535, Notice of Allowance dated Jun. 8, 2012. 8 pages.
Baker, C. A. et al. A new chromatographic procedure and its application to high polymers, J. Chem. Soc., 1956, 2352-2362.
Parallel U.S. Appl. No. 13/600,039; Office action dated Nov. 19, 2012. 24 pages.
Parallel U.S. Appl. No. 13/490,316; Notice of Allowance dated Dec. 10, 2012.
Barman, B.N.; Crude Oil: Liquid Chromatography; 2000; Academic Press. 47 pages.

Table 1

| Evaporative Light Scattering Detector Area Percent | | | | |
|---|---|---|---|---|
| | Saturates | Aromatics | Polars A | Polars B |
| | 23.78 | 32.70 | 9.30 | 34.22 |
| | 22.26 | 31.27 | 9.21 | 38.26 |
| | 21.49 | 30.19 | 9.14 | 39.18 |
| | 23.54 | 32.87 | 9.69 | 33.91 |
| | 21.98 | 29.70 | 9.00 | 39.32 |
| | 21.26 | 29.67 | 8.99 | 40.07 |
| | 21.04 | 30.07 | 8.91 | 39.97 |
| | 23.90 | 34.42 | 9.72 | 31.96 |
| | 20.58 | 28.95 | 8.41 | 42.07 |
| | 20.48 | 32.05 | 7.26 | 40.20 |
| | 21.05 | 33.29 | 8.04 | 37.62 |
| | 21.37 | 34.73 | 8.29 | 35.61 |
| | 21.14 | 35.07 | 8.31 | 35.48 |
| | 21.04 | 34.82 | 8.25 | 35.88 |
| | 21.04 | 34.71 | 8.22 | 36.03 |
| | 21.84 | 34.39 | 8.17 | 36.61 |
| | 20.83 | 34.43 | 8.08 | 36.66 |
| mean | 21.68 | 32.55 | 8.65 | 37.24 |
| s | 1.09 | 2.17 | 0.66 | 2.68 |
| % rsd | 5.01 | 6.65 | 7.66 | 7.19 |

Fig. 6

Table 2

| | Evaporative Light Scattering Detector Area Percent ||||||||
| | Normal-Phase Separation of Maltenes |||| Solubility Separation of Asphaltenes |||
| | Saturate | Naphthene Saturates | Aromatics | Glass Polars | Silica Polars | Cyclohexane Asphaltenes | Toluene Asphaltenes | $CH_2Cl_2$:MeOH Asphaltenes |
|---|---|---|---|---|---|---|---|---|
| | 13.29 | 8.81 | 48.55 | 14.13 | 2.25 | 4.33 | 9.68 | 0.26 |
| | 13.21 | 8.25 | 46.76 | 13.94 | 4.85 | 4.36 | 9.48 | 0.26 |
| | 13.05 | 8.15 | 46.15 | 13.75 | 6.01 | 4.23 | 9.48 | 0.24 |
| | 13.02 | 8.17 | 46.01 | 13.56 | 6.11 | 4.21 | 9.56 | 0.24 |
| | 13.08 | 8.24 | 45.56 | 13.47 | 6.62 | 4.24 | 9.52 | 0.24 |
| | 13.10 | 8.28 | 45.27 | 13.41 | 6.86 | 4.12 | 9.43 | 0.23 |
| | 13.10 | 8.21 | 45.51 | 13.30 | 7.00 | 4.05 | 9.35 | 0.23 |
| | 13.26 | 8.62 | 44.98 | 13.38 | 6.87 | 4.09 | 9.36 | 0.23 |
| | 13.36 | 8.64 | 45.40 | 13.44 | 6.06 | 4.20 | 9.28 | 0.23 |
| | 13.26 | 8.65 | 45.46 | 13.44 | 6.17 | 3.62 | 9.53 | 0.20 |
| mean | 13.17 | 8.40 | 45.97 | 13.58 | 5.88 | 4.15 | 9.47 | 0.24 |
| s | 0.12 | 0.25 | 1.04 | 0.27 | 1.42 | 0.21 | 0.12 | 0.02 |
| % rsd | 0.89 | 2.94 | 2.26 | 1.99 | 24.16 | 5.04 | 1.23 | 7.26 |

Fig. 7

Table 3

| Total Automated SARA Values (ELSD area percent) | | | |
|---|---|---|---|
| Total Saturates | Total Aromatics | Total Resins | Total Asphaltenes |
| 22.10 | 48.55 | 16.38 | 14.27 |
| 21.46 | 46.76 | 18.79 | 14.10 |
| 21.20 | 46.15 | 19.76 | 13.95 |
| 21.19 | 46.01 | 19.67 | 14.01 |
| 21.32 | 45.56 | 20.09 | 14.00 |
| 21.38 | 45.27 | 20.27 | 13.78 |
| 21.31 | 45.51 | 20.30 | 13.63 |
| 21.88 | 44.98 | 20.25 | 13.68 |
| 22.00 | 45.40 | 19.50 | 13.71 |
| 21.91 | 45.46 | 19.61 | 13.35 |
| mean 21.58 | 45.97 | 19.46 | 13.85 |
| s 0.36 | 1.04 | 1.18 | 0.27 |
| % rsd 1.65 | 2.26 | 6.05 | 1.94 |

| Gravimetric SARA Values (weight percent) | | | |
|---|---|---|---|
| Saturates | Aromatics | Resins | Asphaltenes |
| 22.41 | 40.36 | 16.74 | 17.55 |
| 23.78 | 44.52 | 15.92 | 17.17 |
| 22.47 | 41.94 | 15.12 | 15.27 |
| 22.21 | 44.42 | 16.21 | 17.41 |
| 22.27 | 43.16 | 16.86 | 18.35 |
| 23.49 | 43.91 | 15.48 | 17.55 |
| 23.61 | 42.43 | 15.96 | 17.61 |
| mean 22.89 | 42.96 | 16.04 | 17.27 |
| s 0.70 | 1.50 | 0.63 | 0.95 |
| % rsd 3.05 | 3.50 | 3.92 | 5.53 |

Fig. 8

METHODS OF SUCCESSIVE ELUTION OF COMPONENTS OF HYDROCARBONS

This US non-provisional patent application is a continuation of, and claims priority to, U.S. application Ser. No. 13/237,568, filed Sep. 20, 2011, said application incorporated herein in its entirety by reference.

GOVERNMENT LICENSE RIGHTS

This invention was made with government support under FHWA Contract DTFH61-07-D-00005 awarded by the U.S. Department of Transportation. The government has certain rights in the invention, including "march-in" rights, as provided for by the terms of U.S. Department of Transportation under FHWA Contract DTFH61-07-D-00005.

BACKGROUND OF THE INVENTION

Knowing the chemical composition of hydrocarbons (including but not limited to petroleum oils and asphaltic materials) is critical in applications such as improving the performance of bituminous roadways as well as improving refining and oil production efficiency. Certain embodiments of the inventive technology disclosed herein combine innovative features that provide a comprehensive, automated separation of oils in a manner that has not yet been achieved. This separation provides quantitative information about the relative amounts of several fractions using automated, normal phase chromatography coupled with a novel solubility-based separation of asphaltenes, saturates, naphthenes, aromatics, two subfractions of polars, and three solubility subfractions of asphaltenes. The generated data provide valuable insight into compositional differences between different oils and asphalt binders, the internal chemical changes which occur due to aging or processing, and processing generally. The results can be used in establishing compatibility and for predictive modeling, process control, and improving processing efficiency and yield, inter alia.

Adsorption Chromatography Petroleum Separations:

Separating a material into its constituent parts is often necessary in defining its composition. Separations of oils using normal phase chromatography have been around for several decades. One early version of such type of analysis was developed by Corbett who separated asphalts into saturate, naphthene aromatic, polar aromatic and asphaltene fractions. A similar procedure was described by Jewel et al., in which crude oil or asphalt was separated into saturate, aromatic, resin, and asphaltene (SARA) fractions.

Using well known procedures, before these separations can be performed, the oils are usually first separated into two solubility classes by a gravimetric separation utilizing a low polarity hydrocarbon solvent such as isooctane, pentane, or heptane. The soluble material is by definition called the maltenes or petrolenes. The insoluble material is, by definition, called asphaltenes. The gravimetric asphaltenes/maltenes separation typically takes 24 hours. The chromatographic separation of maltenes takes another day. Certain conventional techniques to separate the maltenes employ gravimetric open-column normal-phase adsorption chromatography using polar stationary phases such as activated silica gel or activated aluminum oxide. If the asphaltenes are to be further separated gravimetrically into two solubility subfractions such as cyclohexane soluble and cyclohexane insoluble, it may take an additional day.

Again, using conventional methods, the maltenes are often separated into three fractions by normal-phase liquid chromatography: saturates, aromatics, and resins/polars. The saturates fractions consist of both linear, branched and naphthenic fully saturated organic molecules of low polarity containing carbon and hydrogen and essentially no heteroatoms. A molecule in the aromatics fraction contains mainly carbon and hydrogen, possibly some thiophenic sulfur, few if any heteroatoms, and is distinct from the saturate fraction by containing one or more aromatic rings. The resins and asphaltenes fractions both contain many aromatic rings including highly colored pericondensed aromatic structures, with many polar substituents.

Rod Chromatography: Approaches for SARA separation can be divided into two main groups. The first method that has been widely utilized uses a technique known as thin-layer chromatography (TLC), and when combined with flame ionization detection (FID) becomes semi-automated. This is known as the Iatrocsan method in which capillary thin layer chromatography is conducted with whole oils on silica or alumina rods as a stationary phase, followed by evaporating the elution solvent and then slowly passing the rods through the flame of a flame ionization detector to provide information on the relative amounts of the fractional zones on the rod. The Iatrocsansystem typically elutes the fractions in a sequence of solvents consisting of a linear alkane, cyclohexane, toluene, and dichloromethane:methanol mixtures. However, the Iatrocsan method has severe drawbacks including variable response factors for the different fractions, relatively high amounts of polar compounds retained near the spot location on the TLC rod, and aromatics grouping together to act like resins during separation. The separation is not very repeatable and there is a chronic problem with the strongly adsorbed, asphaltene material which does not migrate up the rod.

Column Chromatography: The second type of method requires initial precipitation of the asphaltenes by dissolving the sample in an excess of an alkane before further separation of the maltenes into the saturate, aromatic, and resin (SAR) fractions by liquid chromatography. Typical methods for the asphaltene separations are described in ASTM D3279, ASTMD4124 or similar. Many variations of the SAR separation have been developed using amino, cyano, or alumina columns including several automated or semi-automated methods utilizing high performance liquid chromatography (HPLC). Radke et al. described a semi-automated, medium pressure liquid chromatography system to separate maltenes involving three analytical columns and three pre-columns in which the pre-columns had to be re-packed between each injection. Variations for automated separations of the maltenes are typically performed using silica gel derivatized with aminopropyl or cyano functional groups. These typically do not provide fully resolved separations of saturates and aromatics and irreversible adsorption occurs on the columns due to resins and soluble asphaltene-type component molecules. A published version of an HPLC SARA method in the laboratory that uses chemically bonded aminosilane stationary phase for an automated SAR separation of crude oil maltenes has been evaluated and, while the authors claim that it also works on bituminous material, no data were presented to support this assertion and attempts to desorb the most polar fractions of asphalt from their system were unsuccessful, resulting in poor recovery and fouling of the column. Fan and Buckley developed a method that used two aminosilane columns. However, HPLC SARA methods that use chemically bonded aminosilane stationary phase of crude oil maltenes result in fouling of the column because of irreversible adsorption of resins. While their system appears to work well for crude oils, the most polar components of the resins fraction of asphalt became irreversibly bonded to the column. Further, the saturates and aromatics fractions are not completely separated in the Fan and Buckley system. It was evident that a new system was needed for asphalt and heavy oils that performs the SAR separation without fouling the column and that allows full recovery of the resins fraction.

This inventive technology, in embodiments, involves a novel combination of two modes of separation/analysis for hydrocarbons such as, e.g., bitumen and oils, including but not limited to petroleum oils, asphalt, coal liquids and shale oils. In embodiments able to quantify asphaltenic constituents, one component of the combined separation is an automated solubility separation in which asphaltenes are precipitated within a ground polytetrafluoroethylene (PTFE)-packed column. This may be referred to as the AsphalteneDeterminator (AD) separation, and may be as described in U.S. Pat. No. 7,875,464 (perhaps supplemented by disclosure herein). In the second component, the material which is not precipitated may be passed onto a series of adsorption chromatographic columns by normal-phase adsorption liquid chromatography for separation into saturates, aromatics, and resins/polars (SAR) components. The SAR (saturates, asphaltenes and resins) separation may utilize three separate adsorption chromatography columns packed with different sorbents. The first column may be packed with high surface energy, non-porous material to reversibly adsorb the very polar and highly aromatic resins materials to keep them from adsorbing irreversibly on the second (and perhaps the third) column. This packing can include a stationary phase such as glass beads, metal particles, ceramics, or other materials (perhaps generally, non-porous, high surface energy materials). The second column may be packed with a weakly adsorbing stationary phase (e.g., an activity reduced stationary phase) such as deactivated silica or amino or cyano functional groups bonded to a silica matrix. The third column may be a highly active, stationary phase such as activated silica or alumina (perhaps an activity enhanced stationary phase). Flow switching and solvent switching valves may be used to provide a separation sequence in which the highly activated stationary phase is not "activity-reduced" (deactivated) during or between separations, allowing for repeated separations without requiring the stationary phases to be changed or discarded between runs. In a step separate from the adsorption chromatography separation of the maltenes, and perhaps after such adsorption chromatography steps are complete, the precipitated asphaltene material on the PTFE column may be re-dissolved using one or more asphaltene solvents (i.e. solvents able to dissolve at least a portion of the precipitated asphaltenes) to provide a solubility distribution profile of the asphaltene material. The result is a combined automated SAR separation coupled with the automated AD (asphaltene determinator) separation to provide a comprehensive characterization of materials.

SUMMARY OF THE INVENTION

When separating materials such as those in asphalt or heavy oils, the most polar compounds become difficult to desorb from a column that also adsorbs the aromatics (or a column that also adsorbs less polar resins compounds). Particular embodiments of the inventive technology disclosed herein include a novel means of removing these materials from solution before the first mobile phase (e.g., heptane solution, with injected hydrocarbon dissolved therein) contacts the porous silica or aluminum oxide based sorbents (or more generally, the active stationary phases) used to adsorb less polar materials. When there is no interest in characterizing the asphaltene component of a hydrocarbon and the asphaltenes are removed therefrom, after asphaltenes are precipitated from oil and filtered using heptane, the resulting heptane solution of maltenes has a brown color due to the presence of pericondensed aromatic compounds that did not precipitate with asphaltenes. After a short period of time, a brown varnish type of coating appears on the surface of the inside walls of the glass container with the heptane maltenes solution (See FIG. 1). Chemically, this varnish material has been found to be similar to the pericondensed aromatic material found in asphaltenes. However, this material remains in the heptane solution during the filtration steps. It is easily desorbed from the glass with toluene or methylene chloride.

This observation has led us to initiate the first use of a column packed with glass beads (generally, a non-porous, high surface energy stationary phase) to precede silica or aluminum oxide columns in a SAR separation to remove the highly pericondensed material so it does not reach the latter, downflow stationary phases. Thus, one primary novelty of this invention is the use of non-porous high surface energy material to reversibly adsorb the most polar resins (and or the most aromatic polar fractions) from maltenes using a liquid chromatography system. The less polar materials can then pass through one or more subsequent columns packed with amino, cyano, silica or alumina stationary phases to separate the saturates, aromatics and remaining resin fractions. This invention is intended to include separation of any hydrocarbon including petroleum material such as residua, bitumen, crude oil, processed materials or products, asphalt, or non-petroleum materials such as additives or rejuvenators, and oil using a column packed with glass beads or other non-porous, high surface energy, typically non-polar surface packing such as metals or ceramics to reversibly adsorb the most highly active pericondensed aromatic resins material prior to any subsequent columns or separation schemes.

Aspects of the inventive technology may also involve a novel combination of a solubility based asphaltene component fractionating and analysis method and an adsorption chromatography method for fractionating and analyzing saturate, aromatics and resins components of an input hydrocarbon.

One advantage of at least one embodiment of the inventive technology is increased accuracy in results relative to amounts of constituents of an input hydrocarbon.

One advantage of at least one embodiment of the inventive technology is an increase in distillate yield of a hydrocarbon that is analyzed (or, more particularly, a sample thereof that is analyzed). Such increase may stem from an enhanced or increased accuracy of results.

One advantage of at least one embodiment of the inventive technology stems from an ability to reuse a stationary phase over a plurality of "runs" through the separator apparatus (each run perhaps separating/analyzing a different hydrocarbon sample) without compromising accuracy of results of second or following "run(s)". Of course, such a capability may result in significant cost savings, as explained further herein.

One advantage of at least one embodiment of the inventive technology is an increase in speed of analysis. Indeed, using certain embodiments of the inventive technology disclosed herein, time from input of a hydrocarbon sample to be analyzed to elution, analysis, and/or generation of results may be less than that found in conventional methods.

One advantage of at least one embodiment of the inventive technology is a reduction in polluting emissions (given a certain distillate yield or a certain hydrocarbon input to be processed).

Other advantages of the inventive technology, in embodiments, may be as disclosed elsewhere in this specification, including the figures.

BRIEF DESCRIPTION OF THE DRAWINGS

FIG. 6 shows Table 1. ELSD Area Percents from the Automated SAR Separation of Maltenes.

FIG. 7 shows Table 2. ELSD Area Percents from the Automated SAR Coupled with the AsphalteneDeterminator Separation of a Whole Residuum.

FIG. 8 shows Table 3. Comparison of Automated and Gravimetric SARA Results for Lloydminster Vacuum Residuum.

DETAILED DESCRIPTION OF THE INVENTION

Figure 1:
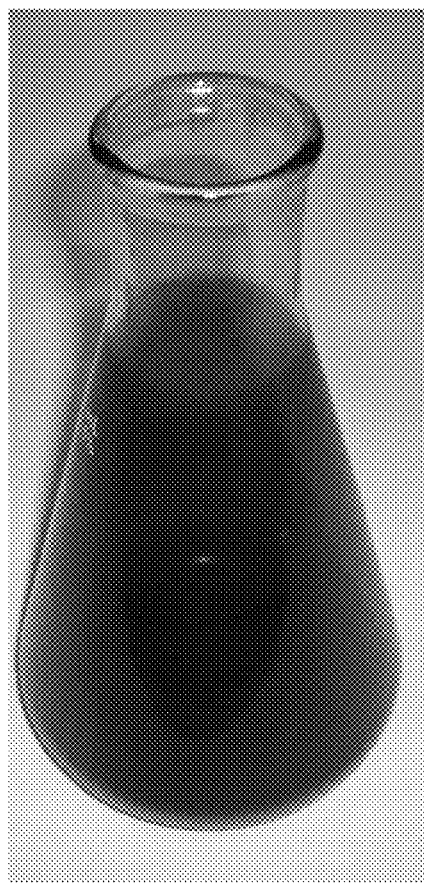
FIG. 1 shows Maltenes Varnish Adsorbed to Glass from Decanted Heptane Solution of Vacuum Residuum Maltenes.

As mentioned earlier, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

A substance, such as a hydrocarbon 1 (whether it be any of a variety of hydrocarbons, including but not limited to oils from fossil, biological or synthetic sources, or derived from biological/renewable oil sources (such as biomass), or oil shale, or even coal (perhaps using a Fischer Tropsch process), may be established or entrained into (and as part of) a first solvent mobile phase 3 via any well known manners (injection, for example). A hydrocarbon may be, as but a few examples, oil, crude oil, a constituent of oil (e.g., maltenes 2), bitumen, binder, light oil, heavy oil, dilbit, opportunity crudes such as heavy sour grades, oils and bitumen, extra heavy oil, high TAN crudes, whether diluted in solvent solution or not. A mobile phase is that which is flowed through at least part of the apparatus, over one or more stationary phases. As such, the term mobile phase, before injection of a hydrocarbon, may be a solvent (e.g., heptane, in one example), but then, after injection, the same mobile phase may be that solvent with a hydrocarbon (e.g., a hydrocarbon sample) dissolved therein, or perhaps with substances desorbed or precipitated therein.

The inert stationary phase 5 (in embodiments with a stationary phase), may be a substantially inert stationary phase, such that any reactivity is only, at the very most, de minimus (i.e., such that any reactivity does not unacceptably affect operational functionality). Typically, it may be nonpolar, and be very low friction. Adsorption to or within the inert stationary phase typically does not occur. An example of sufficiently inert stationary phase media include polytetrafluoroethylene (typically ground or rendered into particles (e.g., beads or smaller) in some manner). Saturates or other constituent components of oil (such as aromatics, resins, and asphaltenes) may be eluted (whether because, as may be the case for saturates, they are not adsorbed onto any stationary phase, or because, as may be the case with aromatics, resins or asphaltenes, they are desorbed from a stationary phase after being adsorbed onto that stationary phase (or, as is the case with asphaltenes, dissolved after being precipitated within a stationary phase). When a component of a hydrocarbon is eluted, it may come out of the column, existing in solution with the mobile phase, and pass through the apparatus to, e.g., an analyzer. Components of a hydrocarbon (e.g., saturates, aromatics, resins and asphaltenes, including subfractions thereof) may be as defined herein, or may have a common, well understood meaning to one of ordinary skill in the relevant art; additional information may be found in the Wiehe and Kennedy reference (cited in the information disclosure statement filed herewith, all of said references incorporated herein in their entirety), in addition to other incorporated, cited references.

Active sorbents 6 (e.g., porous active sorbents such as the active alumina and active silica stationary phases) can be activity reduced (or simply active, if the steps to reduce activity are not performed on the sorbent). Porous as used in this context may imply a porosity that is at or above the lowest porosity (volume of voids over total volume) that still allows for the adsorption intended; its precise value may change depending on the stationary phase used and/or the mobile phase passed over the stationary phase. Typically, an active sorbent will have been heated to remove surface water (e.g., heated to above 100 deg C. but below 500 deg C., or above 110 deg C. to 600 deg. C.). An activity reduced sorbent 7 (e.g., a weakly adsorbing stationary phase such as one including activity reduced silica or alumina), perhaps referred to conventionally as a deactivated sorbent, while still a type of active sorbent, may only be sufficiently active to adsorb resins (that may pass through the non-porous, high surface energy medium (e.g., glass bead stationary phase)), but sufficiently inactive so as to not adsorb aromatics, nor irreversibly adsorb the resins that it does adsorb. Non-porous in this context may imply a porosity that is at or below the highest porosity that still prevents adsorption as intended; its precise value may change depending on the stationary phase used and/or the mobile phase passed over the stationary phase. Activity of the activity reduced stationary phases may have been reduced by exposure of the sorbent (perhaps after the drying operation indicated above) to water or alcohol (perhaps in the form of the methylene chloride:methanol solvent mobile phase). Certain activity reduced stationary phases may be sufficiently inactive without such drying or deactivation procedures. Active stationary phases that have not undergone the deactivation process (such stationary phases may be conventionally referred to as activated media, such as activated alumina or activated silica, which may have only undergone a heat-induced drying), may be, but are not necessarily, referred to as activity enhanced stationary phases 8. Certain active stationary phases may even be a combination of activity enhanced and activity reduced stationary phases. Typically, the active stationary phase is porous, at least more porous than any non-porous, high surface energy stationary phase 8 such as glass beads, or metal or ceramic particles. It is of note that the need for an activity reduced column (e.g., a weakly adsorbing stationary phase) may be eliminated if the non-porous, high surface energy stationary phase has enough non-porous, high surface energy stationary phase (to eliminate the need for the activity reduced column). Further, while silica and/or alumina may be preferred active, porous stationary phases (whether activity reduced (conventionally referred to as deactivated), or activity enhanced (conventionally referred to as activated)), other normal phase chromatography sorbents may suffice, including but not limited to those with aluminum oxide, clay, bonded amino or cyano silica surfaces.

It is of note that the methods, and apparatus, described herein may be only separation methods or apparatus (where the goal is not to analyze a hydrocarbon relative to its constituent fractions, but instead to separate at least one constituent fraction thereof), or they may be only analysis methods (where the goal is not separation of at least one constituent fraction from a hydrocarbon, but rather analysis of a hydrocarbon, such as analysis of percentage composition of one or more of its constituent fractions), or they may be both (analysis and separation). In the case of analysis methods, even where, because a certain constituent of the input hydrocarbon is non-existent (e.g., there are no aromatics or resins), actual eluted amounts are zero, in such a situation, it is still said that the particular constituent that is intended to elute is in fact eluted (it's just that zero amount of it elutes). Diesel fuel, for example, may not have any resins (only saturates and aromatics).

As to the term "fluidic communication", it is of note that "A" can be in fluidic communication (whether controllable or otherwise) with "B" even if there's a non-conduit flow element (e.g., a stationary phase container) between the two. This stems from the fact that flow can, of course, pass through several flow elements (e.g., a stationary phase container(s)), before reaching a downstream flow element. The term container as used herein is a broad term, and includes but certainly is not limited to columnar containers. Generally, fluidic communication implies an ability of a fluid, at least at certain times (where any control devices that may impact that flow are adjusted to allow such flow), to flow from one component to another (via, e.g., any conduit such as tubes or piping). Further, more particularly relative to control of flow (i.e., where two or more components are in controllable fluidic communication), a valve change even several stationary phases upflow from a flow element can divert flow from that downflow flow element. As such, such "remote" flow components can be in controllable fluidic communication. Control of a fluid flow generally implies some sort of device or apparatus (flow control valve 10, such as a flow switching or solvent switching valve, as but two examples) that can allow for flow shut off, flow diversion, flow reduction, flow redirection, and/or flow increase, e.g. A flow switching valve may be a single valve that alone accomplishes a flow switch (e.g., from one mobile phase source to another, whether gradually or in step-wise fashion, and/or redirects that new flow to a different stationary phase container), or it may be one of two or more valves that together accomplish an intended flow switch (e.g., as where one valve shuts off flow from a mobile phase source and, either at that time or later, another valve opens flow from a different mobile phase source). Further, fluidic communication includes, but does not require, controllable fluidic communication, and fluidic communication does not require fluid flow at all times (because controlled fluidic communication can prevent such fluidic communication if, for example, a valve is switched to redirect flow). As to flow control componentry that serves to isolate a flow component (e.g., a stationary phase container such as columnar container), component A may be isolated from components B and C as long as flow through components B or C doesn't go through component A.

Additionally, as mentioned, switching from one mobile phase to another may be done either gradually or in step-wise (more abrupt) fashion. Flow control componentry may be used to accomplish the intended transition. Of course, where a gradual change is desired, shutting off the earlier mobile phase and opening up the later mobile phase may occur more slowly than when a step-wise, abrupt change is desired. Steps involving flow of mobile phase don't mandate any particular transition, but instead include all possibilities given the indicated flow (e.g., from abrupt transition to very gradual transition, including gradients in between the two).

Of course, an important part of one aspect of the inventive technology is the use of a non-porous, high surface energy stationary phase that is upflow of an activity enhanced stationary phase 9. Such may keep the most polar, aromatic resins materials away from the activity enhanced normal phase sorbent 8. The most polar, aromatic resins materials adsorbed onto the non-porous, high surface energy stationary phase are adsorbed reversibly (they can be desorbed easily from the non-porous, high surface energy stationary phase), whereas they would adsorb irreversibly on the activity enhanced porous stationary phase (i.e., such that they could not be desorbed therefrom), but for the non-porous, high surface energy stationary phase.

In particular embodiments of the inventive technology, flow componentry (e.g., valves) that causes resins desorbing mobile phase bypass of a highly activated stationary phase (see step 3 of FIGS. 2 and 4) may be used to prevent deactivation of that highly activated stationary phase. Such may allow for re-use of that stationary phase, or at least obviate a labor intensive, costly "re-activating" step for that stationary phase for it to be used during another run of the apparatus on a different hydrocarbon sample.

A main advantage of certain aspects of the inventive technology is that the apparatus/methods afford complete, and automated, resolution of the saturates and aromatics fractions. Other embodiments, supplemented with asphaltene fractioning steps and components (see FIGS. 4 and 10), resolve one or more of the asphaltene fraction, or resolves the entire asphaltene fraction upon providing compositional information thereabout. Further, one or more of the column packings (i.e., stationary phase media) used in the inventive technology may be less expensive than those typically used by conventional composition analysis schemes (such as very expensive aminopropyl bonded silica, a column of which costs approximately $800-$1000). The silica usable in the inventive method, and the glass beads and PTFE, are much less expensive. Further, conventional schemes often offer only non-resolved, or incompletely resolved, overlapping constituent peaks (e.g., saturates and aromatics peaks may overlap).

In particular embodiments, when there is no interest in characterizing an asphaltene portion of a hydrocarbon (see, e.g., FIGS. 2 and 9), maltenes in solution 2 may be injected into the first solvent mobile phase (from a first solvent source such as a first solvent container of a first solvent). The maltenes (the component of oil that is left after all or substantially all asphaltenes are removed, as by the conventionally known gravimetric precipitation and filtration asphaltene removal method) may thus be dissolved in a low polarity solvent (pentane, heptane, hexane, isooctane as but a few examples), perhaps as a result of the procedure that generates them, and then injected (in solution) into the first mobile phase 3 (which also may be a low polarity solvent such as pentane, heptane, hexane, isooctane as but a few examples). These two solvents may, but need not, be identical. At times, the oil of interest may have so little asphaltenes to start out with that the maltene generation procedure may be skipped; it may then possibly be input in undiluted form (presuming it is not overly viscous). For example, a light crude oil with relatively few asphaltenes could possibly be injected directly, without dilution by a strong solvent. It is of note that the term maltenes 2 (or any other component of oil) can be used in reference to pure maltenes (i.e., undiluted maltenes, with no solvent added), or maltenes in solution (i.e., as dissolved in a solvent, such as low polarity solvent). It is further of note that any of the apparatus may, as should be understood, during operation thereof, further comprise a mobile phase (e.g., a solvent mobile phase) running through the flow conduits of the apparatus; such mobile phase, of course, may have dissolved therein a hydrocarbon; the mobile phase may also have a desorbed hydrocarbon component (saturates, aromatics, resins desorbed from certain stationary phases) or asphaltenes dissolved therein.

Continuing, when there is no interest in characterizing an asphaltene portion of a hydrocarbon, the asphaltenes (when there are asphaltenes) may first be removed from the original hydrocarbon, leaving maltenes (also deemed a type of hydrocarbon). Again, this may be done using a well known procedure (e.g., gravimetric precipitation and filtration). Then, in particular embodiments, a portion of the heptane soluble material (maltenes) in solution may then be injected into the first mobile phase so that it is brought in contact with the non-porous, high surface energy 9 column (e.g., glass bead stationary phase) and columns(s) with active stationary phase 6 (activity enhanced stationary phase 8 and possibly also an activity reduced stationary phase 7). Typically, the only precipitation seen in this scheme is the preliminary, a-columnar (without a column, or without a stationary phase) gravimetric precipitation and filtration of the asphaltenes (to create the maltenes). Reversible chromatographic adsorption of the highly aromatic and polar resins materials on the non-porous, high surface energy column precludes the adsorption of these same materials on the active (typically porous, whether activity enhanced or activity reduced) stationary phase(s) of the column(s) that are downflow (such adsorption would be a highly undesired reversible adsorption, requiring an expensive and time consuming replacement of such active (typically porous) stationary phases). Indeed, at least one aspect of the inventive technology involves successive use, for a different hydrocarbon sample, of a particular bulk quantity of one or more stationary phases (i.e., the very same particles of activity reduced silica, as but one example). Successive solvent mobile phases of increasing solvent strength may be added, with flow control valve(s) being used to bypass particular stationary phases (as particularly described elsewhere in this specification). Separately eluted components (after saturates) may be aromatics and resins.

The SAR separation of asphalt binders was finally enabled by the innovative use of a column filled with glass beads placed before the normal phase separation columns to remove the most pericondensed aromatic asphaltene-like molecules from the maltenes (which do not precipitate with asphaltenes). These molecules can then later be desorbed from the glass beads (or other non porous glass, ceramic, or metal surfaces) using a solvent stronger than heptane. This is important because it is these components which typically, irreversibly adsorb onto normal phase sorbents that are based on silica gel with or without chemical modification, and aluminum oxide. This has been a hindrance to the successful, long term operation of automated SAR separations since a stationary phase with strongly adsorbed components must be discarded after each use because of the components that cannot be desorbed with a strong solvent. Another problem stems from the fact that strong solvents usually deactivate silica or alumina stationary phases such that such deactivated stationary phases are no longer able to fully separate saturates and aromatics. This requires that such stationary phases be discarded and changed frequently. The use of flow components such as switch(es) and/or valve(s) can, in certain embodiments, keep the third mobile phase 20 (e.g., $CH_2Cl_2$:MeOH) off of the activity enhanced stationary phase and prevent it from deactivating such stationary phase.

As mentioned, when there is an interest in using a fully automated, single hydrocarbon sample input procedure to characterize the asphaltenic component of a hydrocarbon, an input that has not had asphaltenes removed therefrom would typically be injected into the first mobile phase. In such case, a relatively strong solvent (e.g., chlorobenzene) that can dissolve the whole sample 12 and keep the asphaltenes in solution may be used to dilute the hydrocarbon 1 of interest because the oil is too viscous to be injected directly in undiluted form). An example is injection of 20 uL of a 10% (w/v) solution that includes 2 mg of a residuum or asphalt binder (bitumen). Even where an undiluted hydrocarbon is diluted in a solvent, and that solution is then input into a mobile phase, it is still said that a hydrocarbon is input into that mobile phase. If the oil were sufficiently non-viscous (sufficiently liquid), then a direct injection of 2 mg may suffice. After injection of the hydrocarbon (via controllable hydrocarbon input 65, where controllable merely implies an ability to start and stop the input, or merely allow input of a limited amount of hydrocarbon), the first mobile phase, which ideally may be any low polarity solvent (including, of course, a nonpolar solvent) that can precipitate some of the asphaltenes within the inert stationary phase, should suffice. Examples may include but are not limited to: hexane, heptane, isooctane and pentane. While a low polarity first mobile phase (for methods that characterize the asphaltenic fraction) may be preferred, it may not be necessary, as the critical requirement for this solvent is that it precipitates any portion of the sample (e.g., the asphaltenic portion). It is of note that the first mobile phase is preferably an alkane solvent regardless of whether the input hydrocarbon is a maltene or whether it includes asphaltenes. However, when the protocol involves asphaltene separation (for resolution thereof, as shown perhaps in FIGS. 4 and 10), the first mobile phase 3 should additionally be able to precipitate asphaltenes within the inert stationary phase.

The SARA procedure (saturates, aromatics, resins and asphaltenes) may involve a novel combination of two modes—an asphaltenic mode (which may be non-chromatographic and instead, solubility based), and an adsorption chromatography mode dedicated to the separation and/or analysis of saturates and possibly also aromatics and resins—for separation/analysis of oils including but not limited to petroleum oils, bitumen, asphalt, coal liquids and shale oils. In embodiments that resolve asphaltenic constituents, an initial step may be an automated solubility separation in which asphaltenes are precipitated within a ground polytetrafluoroethylene (PTFE)-packed column using a non-polar solvent, perhaps as disclosed in U.S. Pat. No. 7,875,464, or as disclosed herein (said patent incorporated herein in its entirety). In the second component, the material which is not precipitated in the first step may be passed onto a series of adsorption chromatographic columns for separation by normal-phase, adsorption, liquid chromatography into saturates, aromatics, and resins/polar aromatics (SAR) or other similar (e.g., naphthenic polar) components. The SAR separation may utilize three separate adsorption chromatography columns packed with different sorbents. The first adsorption column may be packed with high surface energy, non-porous material 9 to reversibly adsorb the very polar and highly aromatic resins materials to keep them from adsorbing irreversibly on the second downflow column (and/or other downflow column). The second adsorption column may be packed with a weakly adsorbing stationary phase 7 (activity reduced silica or alumina, as but two examples) that adsorbs the resins that pass through the first adsorption column. The third adsorption column may be packed with a highly active stationary phase 8 such as activity enhanced stationary phase 8 (e.g., activated silica or alumina, as but two examples), for separation of the aromatic components from the saturated hydrocarbon components. Flow control componentry (e.g., flow control valves 10) such as flow direction valves and/or solvent switching valves may be used to provide a separation sequence in which a highly activated stationary phase is not deactivated (or have its activity reduced) during or between separations, allowing for repeated separations without requiring the stationary phases to be regenerated, changed, or discarded between runs.

Briefly, in certain applications, where there is an interest in using a fully automated, single hydrocarbon sample input procedure to characterize the asphaltenic component of a hydrocarbon (among characterizing other components), a hydrocarbon solution of whole oil 12 (i.e., that includes asphaltenes) in a strong solvent may be injected into a first mobile phase (heptane is one type of such mobile phase; other examples are listed herein) from a first mobile phase source 60. Thereafter, the asphaltenes precipitate within the inert stationary phase 5 (e.g., within the column with substantially inert stationary phase such as PTFE therein). The term "precipitation within a stationary phase", stationary phase container, or column indicates precipitation in the solvent mobile phase (e.g., in heptane) within the pores of the bed of the stationary phase (e.g., PTFE). Such precipitation is non-chromatographic. Steps, and components that follow (other than those related to the inert stationary phase or the asphaltenes themselves, or the use of solvent mobile phases specifically to dissolve precipitated asphaltenes), may be as seen in those embodiments that are not designed to also elute (and possibly also analyze) asphaltenes. The first mobile phase soluble material may continue on to the non-porous, high surface energy stationary phase and the remaining stationary phases (e.g., active stationary phases 6, whether activity reduced 7 or activity enhanced 8 or a combination of the two). Adsorption chromatograph occurs in such containers (e.g., columns). Aliphatic hydrocarbon material (saturates) may pass through all columns and elute first. The activity enhanced column (e.g., activity enhanced, or activated, silica) prevents the aromatics from eluting with the saturates (because the aromatics are adsorbed, reversibly, onto the activity enhanced column). The non-porous, high surface energy stationary phase 9 (e.g., glass bead) and any activity reduced stationary phase column 7 (e.g., activity reduced silica or activity reduced alumina, as but two examples), adsorb the resins material (perhaps referred to elsewhere herein as polars material). The most aromatic and polar resins materials are reversibly adsorbed onto the non-porous, high surface energy stationary phase instead of irreversibly adsorbed onto any of the active stationary phases (whether activity reduced or activity enhanced) that are downflow of it. Flow control valve(s) 10 may then be used to isolate the first column (the inert material column, which may preferably include PTFE) and the non-porous, high surface energy column. A second solvent mobile phase 19 (e.g., toluene or similar, which is stronger than the first solvent mobile phase), from a second solvent source 61, may then be backflushed through the active columns, but not the non-porous, high surface energy column, nor the inert stationary phase column; this backflush elutes aromatics. It is of note that any backflush or backflow of a mobile phase over a stationary phase typically involves backflow through that container (e.g., column), as where the flow direction through the column (e.g., of the second and third mobile phase) is opposite the flow direction of the first mobile phase through the column. While FIGS. 9 and 10 don't show such backflow (indeed, they show forward flow through the stationary phases), they do show a reversed order of flow of the second and third mobile phases as compared with the first mobile phase (for example, the second mobile phase hits the activity enhanced stationary phase before it hits the activity reduced stationary phase). During such reversed order of flow of the second or third mobile phases, either forward or back flow through the individual stationary phases is possible in embodiments of the inventive technology. Then, using a flow control valve(s), a third solvent mobile phase 20 (methylene chloride:methanol, chloroform: methanol, methylene chloride:ethanol, trichloroethane: methanol, cyclohexanone:methanol, as but a few examples), from a third solvent source 62, which is stronger than the second (and first) solvent mobile phases, may then be backflushed through the non-porous, high surface energy column and any activity reduced stationary phase that may be used, but not through the activity enhanced stationary phase (because the alcohol, e.g., methanol, would deactivate it), nor through the inert stationary phase. This elutes the polars (resins) that were adsorbed onto the non-porous, high surface energy column and any activity reduced stationary phase that may be used (perhaps resulting in two resins peaks).

Such columns—the non-porous, high surface energy stationary phase column, the activity enhanced stationary phase column, and any activity reduced stationary phase column that may be used—are then isolated using flow control valve(s), and the asphaltenes (or a portion thereof) of the inert stationary phase column (e.g., PTFE column) that were earlier precipitated within the inert column are dissolved using at least one asphaltene solvent. It is of particular note that the term asphaltene solvent is a solvent that can dissolve one or more asphaltenic components (i.e., at least a portion of asphaltenes) of a hydrocarbon. In order to gain more information on the compositions of different asphaltenes, solvents of increasing strength may be used. For example, a first asphaltene solvent mobile phase, from a first asphaltene solvent mobile phase source 22 (for the asphaltene dissolution stage) may be cyclohexane, with a second asphaltene solvent mobile phase from a second asphaltene solvent mobile phase source 23 being toluene, and a third (from third asphaltene solvent mobile phase source 24) being methylene chloride:methanol, with each dissolving a different asphaltene subfraction, resulting in the passage of this subfraction(s) to analysis componentry, if desired. The asphaltene dissolution protocol may be as disclosed in U.S. Pat. No. 7,875,464. Alternate mobile phases include but are not limited to benzene, xylenes, mixtures of cyclohexane and heptane, mixtures of toluene and heptane, chloroform, cyclohexanone. The result, in particular embodiments, is a fast, accurate method to fully characterize the composition of oils.

Figure 2:
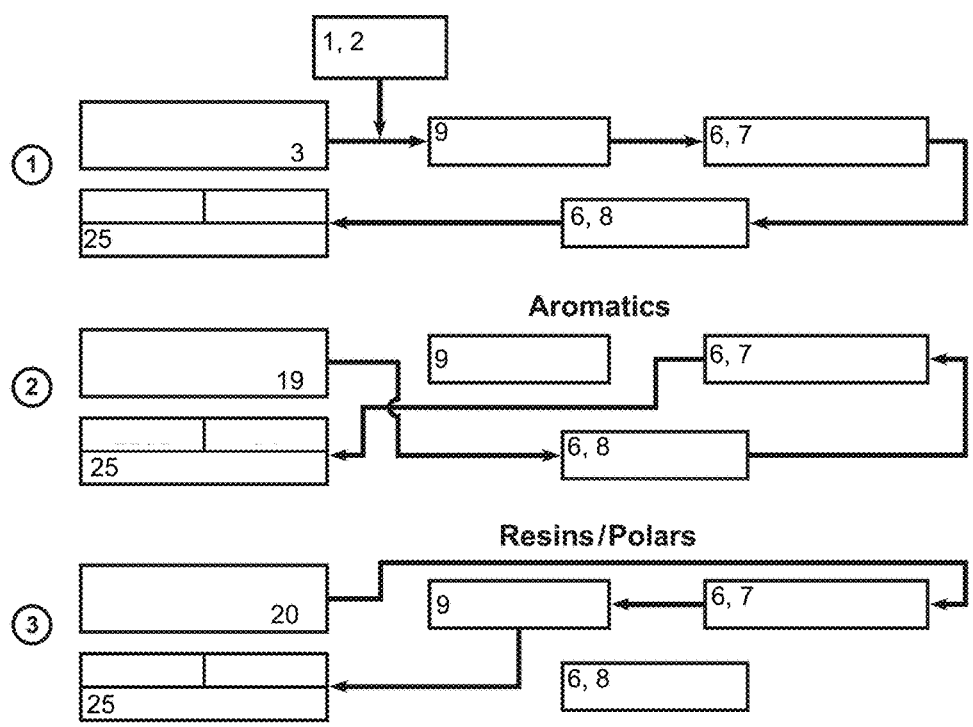
FIG. 2 shows a Flow Diagram for the Automated SAR Separation of Maltenes.
Figure 4:
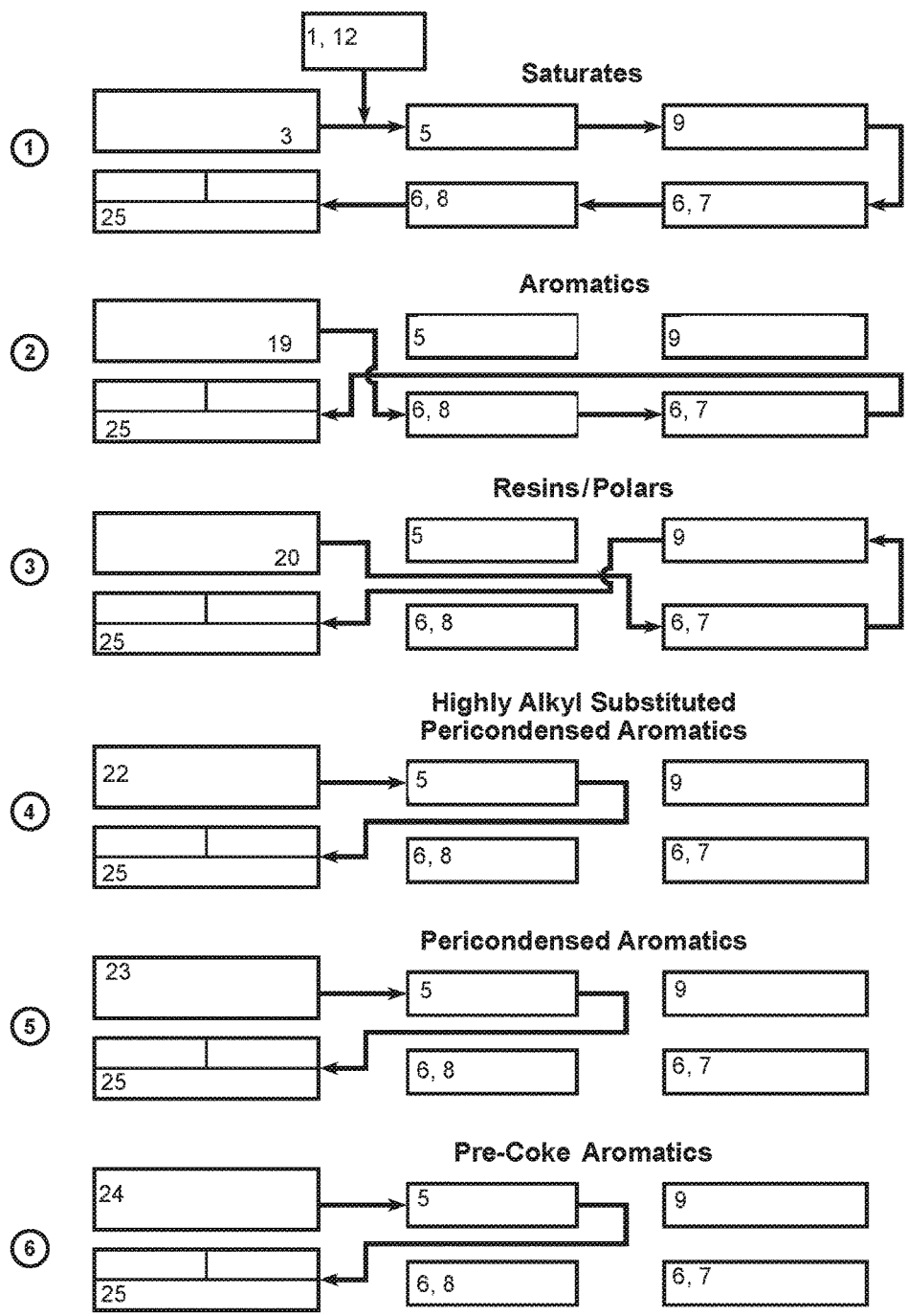
FIG. 4 shows a Flow Diagram for the Automated SAR Coupled with the AsphalteneDeterminator.
Figure 9:
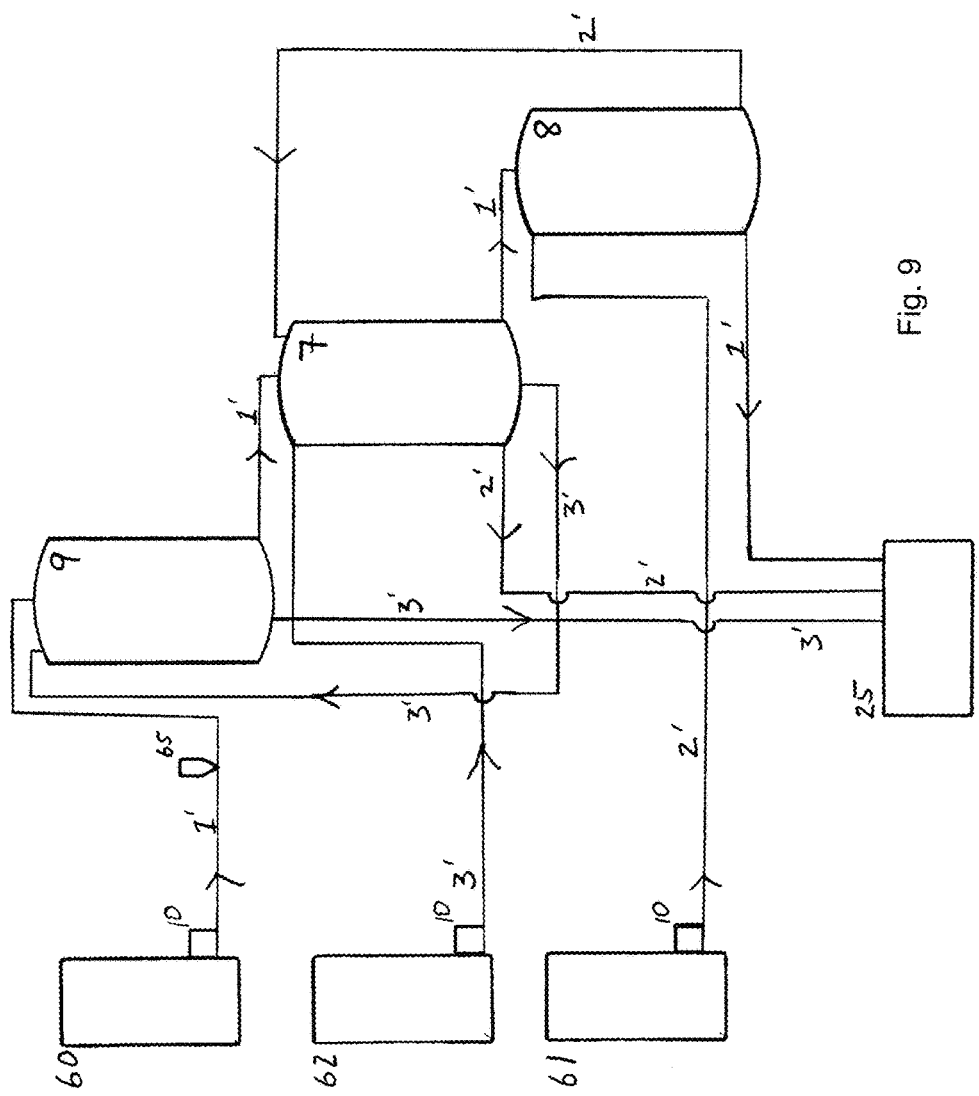
FIG. 9 shows an example of an embodiment of an apparatus particularly suited for SAR resolution. The primed numbers correlate with steps of FIG. 2.
Figure 10:
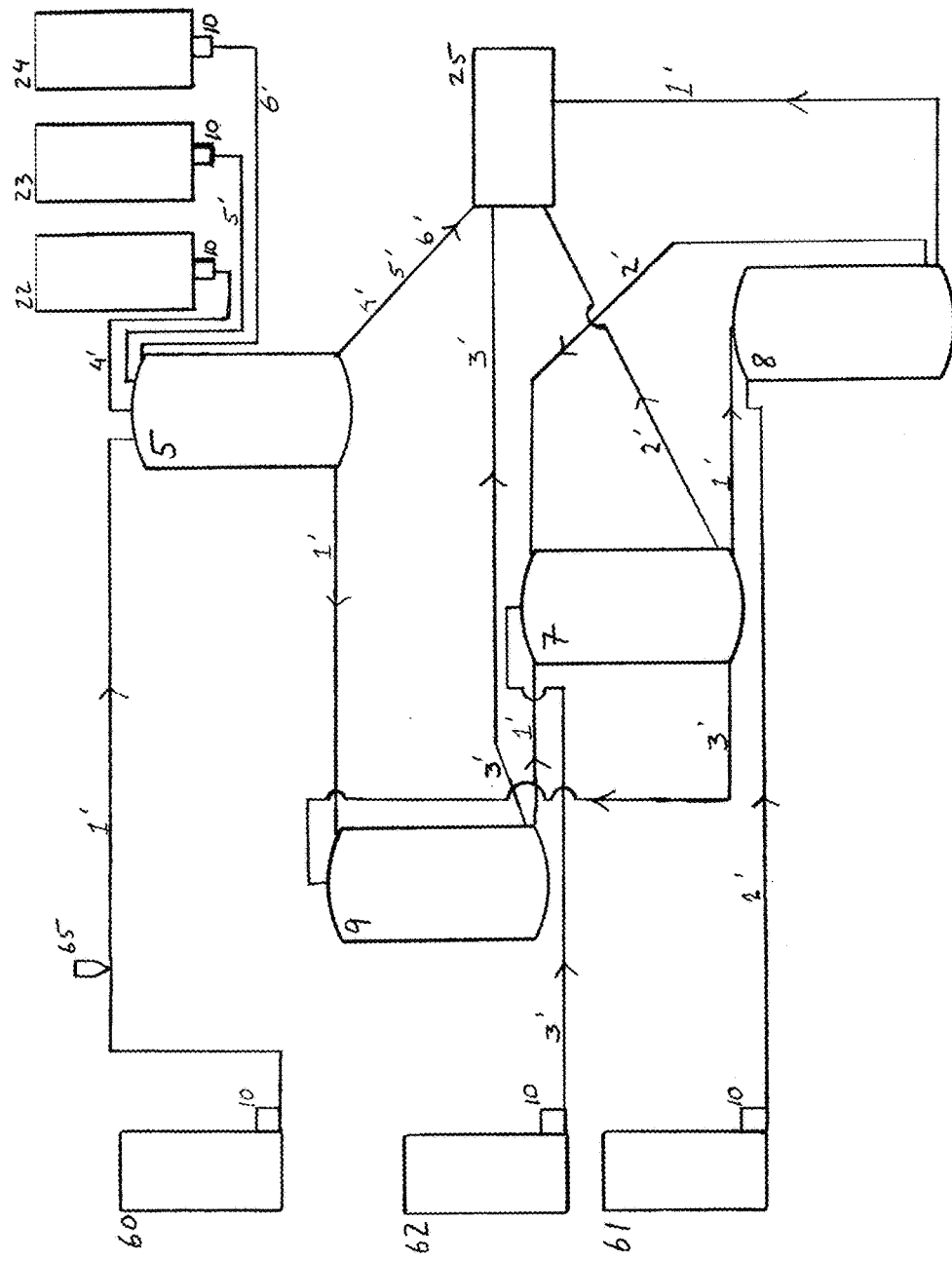
FIG. 10 shows an example of an embodiment of an apparatus particularly suited for SARA resolution. The primed numbers correlate with steps of FIG. 4.

It is also of note that at times, only information regarding one constituent fraction of the oil, such as the saturates fraction, may be of interest. In such case, perhaps additional steps and components (e.g., additional mobile phases) that are non-essential to gleaning the desired information may be eliminated from the procedure. Further, regardless of whether the inventive method involves analysis (e.g., compositional determination) of asphaltenes, the need for a weakly adsorbing stationary phase (activity reduced stationary phase) may be obviated if a sufficiently large amount of the non-porous, high surface energy stationary phase is used. If such sufficiently large amount of the non-porous, high surface energy stationary phase is used, in certain applications, the activity reduced stationary phase may possibly be eliminated, resulting in a process that still provides acceptable resolution for the intended application. It is of note that FIGS. 2 and 4 show steps in at least a few embodiments of the inventive technology. As mentioned, depending on the goals of the separation/analysis, certain steps (e.g., the aromatics and resins elution steps (steps 2 and 3 of FIGS. 2 and 4), and the asphaltene elution steps (steps 4-6 of FIG. 4)) may be selectively, perhaps individually, eliminated. Further, depending on the goal(s) of the procedure, certain components may not be required. For example, if there is no interest in resolving an asphaltene component, then the inert stationary phase may not be necessary. If one is interested only in the highly alkyl substituted pericondensed aromatics fraction of the asphaltenes, then the other alsphaltene solvents may be eliminated. Also, as mentioned, in applications where there is interest in resolving an asphaltene component, if enough of the inert stationary phase is used, the activity reduced stationary phase may be eliminated. It is also of note that the diagrammatic representations of the SAR and SARA separation and analysis apparatus as shown in FIGS. 9 and 10, respectively, each show only one possible way of using flow control valves so as to achieve the flow of the mobile phases as intended (e.g., to their intended stationary phases). Upon presentation of this disclosure, other arrangements could be designed by one of ordinary skill in the relevant art.

As should be understood, aspects of the inventive technology may involve high surface energy materials (e.g., the non-porous, high surface energy media, such as glass beads, of one of the stationary phase columns). Such high surface energy material will have a surface energy (perhaps otherwise known as surface free energy or surface tension) of greater than or equal to 100 mN/m; other types of such material may perhaps have only greater than or equal to 40 mN/m. Generally, high surface energy material implies a surface energy greater than or equal to 40 mN/m. Onto this high surface energy material is adsorbed components of the oil (such as very aromatic material, inter alia) that themselves typically have surface energies that are from about 40-100 mN/m. As to the weakly adsorbing stationary phase (when used), such as activity reduced silica or activity reduced alumina (as but two examples)—in one example it is any stationary phase (such as a porous sorbent) that is activity reduced via exposure of the sorbent (perhaps after a surface drying via heating operation indicated elsewhere in this description) to water or alcohol (perhaps in the form of the methylene chloride:methanol solvent mobile phase). It is also of note that where the viscosity of an input oil is greater than, e.g., 20 cP, there may be a need to dilute such oil with a solvent before injecting it into the first mobile phase.

Often, the purpose of any of the inventive methods disclosed herein is analysis of the input hydrocarbon; typically, that analysis means a characterization in some manner (typically numerically) of one or more of the various constituents of the input hydrocarbon (e.g., saturates, aromatics, resins, naphthenes, asphaltenes, subfractions of polars, and solubility subfractions of asphaltenes, as but a few examples). Often, that characterization relates to the amount of the constituent(s) of interest in the hydrocarbon, whether on a percentage or other basis, where that constituent(s) of interest is eluted from the apparatus. Analysis componentry 25 may include, but is not limited to well known detectors, such as ELSD (evaporative light scattering detector), optical absorbance (which include UV and visible), refractive index, CAD (charged aerosol detector), and other spectrometers. Information gleaned from analysis can additionally, or instead, aid in assessing compatability of the oil or hydrocarbon material associated with the input hydrocarbon (e.g., maltenes, or perhaps one containing asphaltenes) conducting predictive modeling, selecting feed (unprocessed hydrocarbon input) for process optimization, and effecting process control. It is also of note that current methods, whether because of unresolved peaks of eluted materials or for other reasons, do not afford the accuracy afforded by the instant inventive technology. Further, high costs associated with non-reusable stationary phases may force some refineries at times to forego any SAR or SARA determination whatsoever. Regardless, refineries (a term that includes but certainly is not limited to laboratories that analyze hydrocarbons) using conventional technologies are processing hydrocarbons with limited information about them (e.g., about coking onset) and their compositional makeup. As such, in order to avoid coke formation, or form only a small amount of coke during processing (or in order to avoid fouling of catalysts and/or heat exchanges, or only cause minimal fouling, or in order to avoid or minimize formation of emulsions in desalters, all during or as a result of processing), relatively conservative processing conditions are used. Indeed, the lack of information about the unprocessed (or partially processed) input hydrocarbon causes process operators to not produce as much end product(s) (e.g., gasoline, fuel oil, lubricating oils, diesel fuel, kerosene, jet fuel, tar, heavy fuel oil and asphalt) as could possibly be produced if they had more accurate, reliable information regarding compositional makeup, and could "push", or further adjust processing conditions (residence time, pressure, temperature, catalyst use, etc.), to produce more product while still avoiding coke formation (or only forming an small amount of coke) or experiencing other undesired outcome (e.g., any or too much fouling, unacceptable amounts of emulsion generation in desalters). The more accurate the information, the more efficient the process is because, e.g., coke onset estimation becomes more accurate as a result. As such, particular embodiments of the inventive technology disclosed herein enable greater end product production—a supplemental end product, or an end product not produced using conventional technology for a given hydrocarbon processor input (refinery input). In this way, carbon dioxide and other undesired emissions (such as SOx, NOx, as but a few examples, all generally termed pollutants) can be reduced for a given production of a hydrocarbon end product (or a supplemental amount of oil can be produced for a certain amount of emissions, or for a given hydrocarbon processing expenditure, or for a given emissions allotment, allowance or expenditure). Such efficiency has obvious cost savings implications and, if a cap and trade scheme is ever legislated, will result in emissions credits associated with this "reduced emissions per produced end product" that, having a monetary value (estimated in 2011 to be from $20/ton to $140/ton, which may indeed change depending on the market conditions), can be traded on the market. Indeed, the owner of the inventive technology claims that market value, in addition to the supplemental oil per hydrocarbon input, or per emissions output afforded upon use of the inventive technology, inter alia.

As an example of calculations that suggest the magnitude of costs savings attributable to the inventive technology based on an estimate of 2.3 million barrels of heavy ends per day of thermal cracking and coker feed that can be produced from distillation operations in the U.S., an industry-wide 1% increase in distillate yield (end product) from safely cutting deeper into a heavy oil during distillation (perhaps a low end, conservative estimate) would result in about 23,000 bpd of supplemental end product, worth approximately $230,000/day, assuming a differential price between residua and distillate of $10/bbl. Further, there would be significant energy savings involved using aspects of the inventive technology, as coking operations use about 166,000-258,000 Btu per barrel of feed (USDOE 1998). For each 1% decrease in thermal cracking and coker feed (near 23,000 barrels per day in 2011, (USEIA 2011)), there would be a potential energy savings of about 3.8-5.9 billion Btu for residua that do not need to be heated for coking, since they will have been recovered in an optimized distillate stream. This also corresponds to a lowering of carbon dioxide from fuel that is not burned in coking operations. Residual fuel used as the heat source produces about 174 pounds of carbon dioxide per million Btu generated. Thus, in the U.S., the reduction in carbon dioxide emissions for each 1% industry-wide distillation efficiency improvement may be about 331-515 tons per day (2011 figures). Given the above-mentioned monetary per ton emissions estimate ($20-$140/ton), at 515 tons/day (188,000 tons/yr), which certainly could increase, market value for avoided $CO_2$ emissions (valued according to market value of traded emission credits) could be $3,760,000/yr up to $26,320,000/yr for each 1% gain in efficiency. So, a 5% efficiency gain would yield $18,800,000 to $131,600,000/yr in $CO_2$ emission value. Of course, actual savings/costs/value could be greater (including the 1% gain); these are merely estimates.

Laboratory Results:

The following laboratory conditions and results, while presented using particular data, are not intended to limit the scope of the inventive technology.

Automated SAR Separation:

The flow diagram for an example SAR separation that has been successfully demonstrated with repeat injections is illustrated in FIG. 2. For the normal phase chromatography method, 190 μL portions of 1% (wt/vol) heptane maltenes dissolved in heptane are injected into the system. Solvent flow rates are 2 mL/min. Following Step 1 in FIG. 2, the saturates elute with heptane through a glass bead column, deactivated (activity reduced) silica column, and activated (activity enhanced) silica column. The highest surface energy resins adsorb on the glass beads, and other resins adsorb to the deactivated silica column. The aromatics may adsorb on the deactivated silica column and partially on the activated silica column. Step 2 may be a back flush with toluene through the deactivated silica and activated silica columns to elute the aromatics. The final step may involve back flushing the deactivated silica and glass bead columns with $CH_2Cl_2$:MeOH (98:2 v:v) to elute the resins molecules. The entire system is then regenerated with an initial toluene back flush followed by heptane. Because the activated silica column is never contacted with methanol, it does not become deactivated and thus it is suitable for many repeat separations without requiring stationary phase reactivation or repacking.

The silica used for the example is grade 62, 60-200 mesh, 150 Å from Sigma Aldrich activated at 120° C. overnight. Glass beads are 150-212 μm unwashed from Sigma. The separation is conducted at 30° C. with a column heater and it utilizes automated 4-port and 6-port switching valves to direct the flows as illustrated in FIG. 2.

The solvent switching sequence used is provided below. Column 1 is packed with glass beads, column 2 is packed with silica gel that becomes deactivated (activity reduced) by contact with the methylene chloride:methanol (98:2 v:v) solvent and is designated the deactivated (DA) (activity reduced) silica gel column, and column 3 is the activated (A) (activity enhanced) silica gel column.

1. 0-25 minutes, heptane through columns 1, 2, and 3.
2. 25-48 minutes, toluene back flush through columns 3 and 2.
3. 48-70 minutes, methylene chloride:methanol (98:2 v:v) back flush through columns 2 and 1.
4. 70 begin toluene followed by heptane flushing to prepare for next injection.

Figure 3:
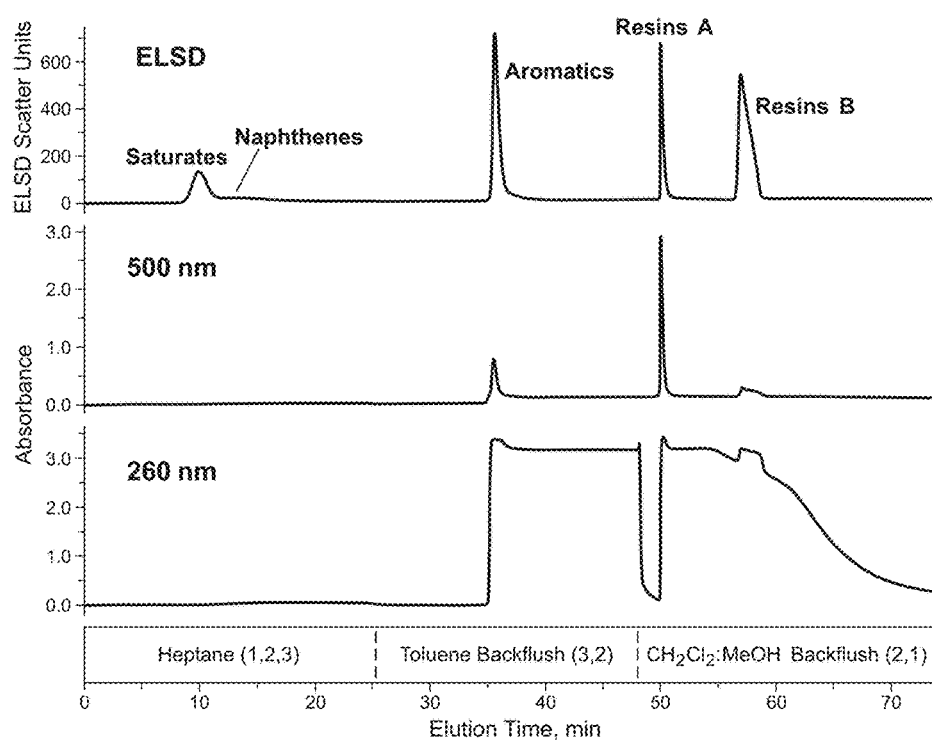
FIG. 3 shows a Separation Profile for the Automated SAR Separation of Maltenes.

A separation profile of 2 mg residuum in heptane maltenes is provided in FIG. 3. An evaporative light scattering detector (ELSD), a type of analysis equipment, is used for quantifying fractions while optical absorbance detection at 260 nm provides evidence that aromatics are not eluting with the saturates fraction, and 500 nm absorbance detects the elution of pericondensed aromatic molecules in the aromatics and resins fractions. The ELSD area percent corresponds to weight percent of material. In this separation, there are two resins subfractions, the glass bead resins which elute first, followed by deactivated silica resins. The saturates fraction which elutes with heptane consists of a single large peak followed by a broader shoulder peak. This latter peak probably is due to naphthenes and could contain small amounts of highly alkyl substituted structures. It could also olefins, or very highly aliphatic substituted aromatic components. The toluene back flush elutes the aromatics. Resins/polars are eluted with methylene chloride:methanol (98:2 v:v). Alternative solvents or similar combinations of sorbents could be used in variances of this separation.

The repeatability of the separation from a series of injections of 2 mg heptane maltenes is provided in Table 1 (See FIG. 6). The consistent area percent for the saturates fraction is an indicator that the activated silica column is not becoming deactivated.

Automated SAR/AD Combined Separation:

A main feature of this invention is coupling the automated SAR with the automated AsphalteneDeterminator separation which is used to separate the asphaltenes into three solubility fractions consisting of highly alkyl substituted pericondensed aromatics, alkyl substituted pericondensed aromatics, and pre-coke/polar aromatics (14-17). The flow schematic for the combined SAR separation coupled with the AsphalteneDeterminator separation is provided in FIG. 4. The solvent switching sequence is provided below. The last three columns are the same as those used in the SAR separation described previously. A column packed with 40-60 mesh polytetrafluoroethylene (PTFE) is place before these columns for the initial on-column precipitation of asphaltenes on an inert stationary phase. Column 1 is packed with ground PTFE, column 2 is packed with glass beads, column 3 is packed with silica gel that becomes deactivated by contact with the methylene chloride:methanol (98:2 v:v) solvent and is designated the deactivated (DA) (activity reduced) silica gel column, and column 4 is the activated (A) (activity enhanced) silica gel column.

Figure 5:
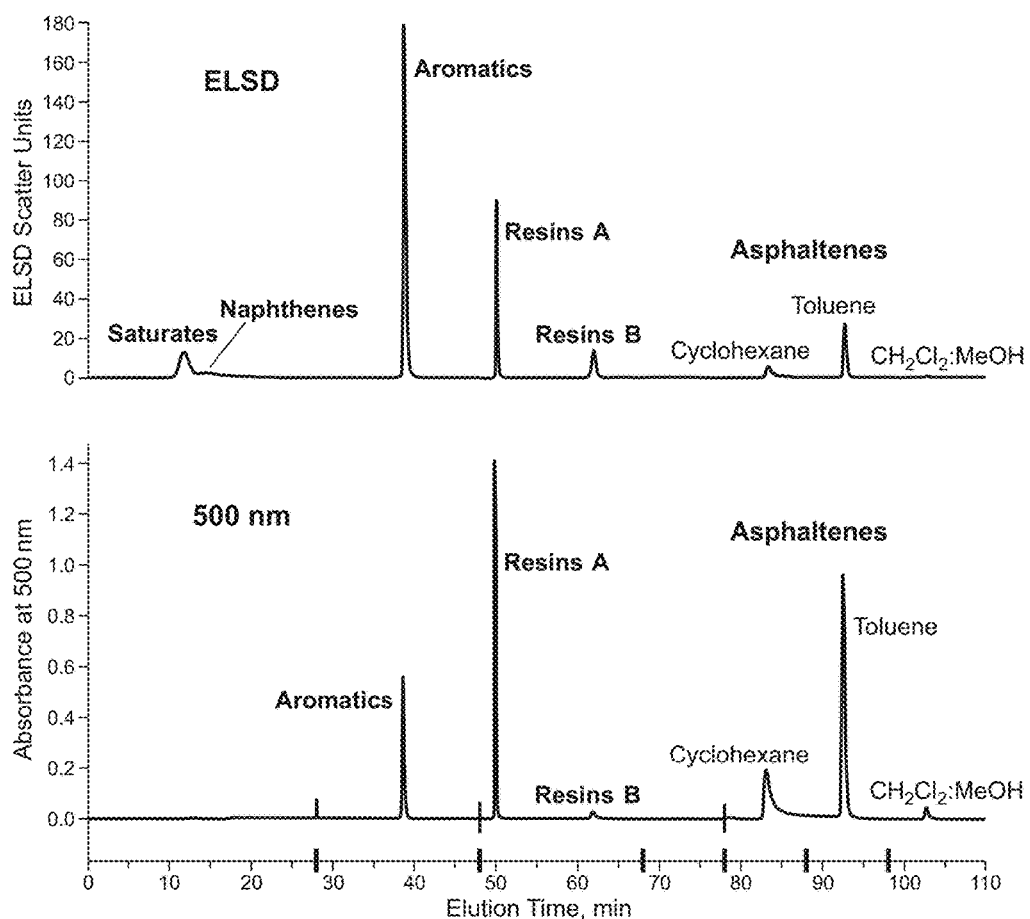
FIG. 5 shows a Separation Profile for the Automated SAR Coupled with the AsphalteneDeterminator for the Separation of a Whole Residuum.

1. 0-28 minutes, heptane forward flow through columns 1, 2, 3, and 4.
2. 28-48 minutes, toluene back flush (or backflow) through columns 4 and 3.
3. 48-68 minutes, methylene chloride:methanol (98:2 v:v) back flush through columns 3 and 2.
4. 68-78 minutes, toluene back flush followed by heptane back flush through columns 4, 3, and 2.
5. 78-88 minutes, cyclohexane forward flow through column 1
6. 88-98 minutes, toluene forward flow through column 1
7. 98-108 minutes, methylene chloride:methanol (98:2 v:v) forward flow through column 1
8. 108, minutes, begin toluene followed by heptane back and forward flow/flush to prepare for next injection The separation profile for 20 uL of a 10% (wt·vol) solution (2 mg) of Lloydminster vacuum residuum in chlorobenzene with the coupled SAR/AD system is illustrated in FIG. 5. By automating the entire process in a comprehensive scheme using only a 2 mg whole sample without prior removal of asphaltenes, the entire separation can be performed in less than two hours.

Repeat injection data for 2 mg portions of Lloydminster vacuum residuum in chlorobenzene are provided in Table 2 (See FIG. 7). The data illustrate that the results are consistent for a series of repeat injections. The repeatability of the relative saturates peak area percent indicates that the activated silica gel packed column remains activated.

Gravimetric separations data for Lloydminster vacuum residuum were compared with the automated method data. The data from the automated separation compared favorably with data generated using a gravimetric, open column procedure using 35 g of the same activated silica gel used in the activated silica column for the automated separation (grade 62, 60-200 mesh, 150 Å from Sigma Aldrich activated at 120° C. overnight) to separate 0.35 g maltenes using 400 mm long×19 mm ID glass column, following gravimetric precipitation of heptane asphaltenes (Table 3—see FIG. 8).

Additional Information: As can be easily understood from the foregoing, the basic concepts of the present invention may be embodied in a variety of ways. It involves both hydrocarbon constituent separation and/or analysis techniques as well as devices to accomplish the appropriate separation and/or analysis. In this application, the separation and/or analysis techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "analyzer" should be understood to encompass disclosure of the act of "analyzing"—whether explicitly discussed or not—and, conversely, were there effectively disclosure of the act of "analyzing", such a disclosure should be understood to encompass disclosure of an "analyzer" and even a "means for analyzing" Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the separation and/or analysis devices/apparatus as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

In addition and as to computer aspects and each aspect amenable to programming or other electronic automation, the applicant(s) should be understood to have support to claim and make a statement of invention to at least: xv) processes performed with the aid of or on a computer as described throughout the above discussion, xvi) a programmable apparatus as described throughout the above discussion, xvii) a computer readable memory encoded with data to direct a computer comprising means or elements which function as described throughout the above discussion, xviii) a computer configured as herein disclosed and described, xix) individual or combined subroutines and programs as herein disclosed and described, xx) a carrier medium carrying computer readable code for control of a computer to carry out separately each and every individual and combined method described herein or in any claim, xxi) a computer program to perform separately each and every individual and combined method disclosed, xxii) a computer program containing all and each combination of means for performing each and every individual and combined step disclosed, xxiii) a storage medium storing each computer program disclosed, xxiv) a signal carrying a computer program disclosed, xxv) the related methods disclosed and described, xxvi) similar, equivalent, and even implicit variations of each of these systems and methods, xxvii) those alternative designs which accomplish each of the functions shown as are disclosed and described, xxviii) those alternative designs and methods which accomplish each of the functions shown as are implicit to accomplish that which is disclosed and described, xxix) each feature, component, and step shown as separate and independent inventions, and xxx) the various combinations and permutations of each of the above.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC*, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A method of successively eluting components of a first hydrocarbon sample and then a second, different hydrocarbon sample, said method comprising the steps of:
    entraining said first hydrocarbon sample into and as part of a first run amount of a first solvent mobile phase, said first solvent mobile phase having a first solvent strength;
    passing said first run amount of said first solvent mobile phase over a particular bulk quantity of a non-porous, high surface energy stationary phase;
    reversibly adsorbing resins materials of said first hydrocarbon sample onto said particular bulk quantity of said non-porous, high surface energy stationary phase;
    passing said first run amount of said first solvent mobile phase over a particular bulk quantity of an active stationary phase;
    eluting a saturates component of said first hydrocarbon sample;
    passing a first run amount of a second solvent mobile phase over said particular bulk quantity of said active stationary phase, said second solvent mobile phase having a second solvent strength that is greater than said first solvent strength;
    eluting an aromatic component of said first hydrocarbon sample;
    passing a first run amount of a third solvent mobile phase over said particular bulk quantity of said non-porous, high surface energy stationary phase, said third solvent mobile phase having a third solvent strength that is greater than said second solvent strength;
    eluting a resins component of said first hydrocarbon sample;
    entraining said second, different hydrocarbon sample into and as part of a second run amount of said first solvent mobile phase;
    passing said second run amount of said first solvent mobile phase over said particular bulk quantity of said non-porous, high surface energy stationary phase;
    reversibly adsorbing resins materials of said second, different hydrocarbon sample onto said particular bulk quantity of said non-porous, high surface energy stationary phase;
    passing said second run amount of said first solvent mobile phase over said particular bulk quantity of said active stationary phase;
    eluting a saturates component of said second, different hydrocarbon sample;
    passing a second run amount of said second solvent mobile phase over said particular bulk quantity of said active stationary phase;
    eluting an aromatic component of said second, different hydrocarbon sample;
    passing a second run amount of said third solvent mobile phase over said particular bulk quantity of said non-porous, high surface energy stationary phase; and
    eluting a resins component of said second, different hydrocarbon sample.

2. A method of successively eluting components of a first hydrocarbon sample and then a second, different hydrocarbon sample as described in claim 1 wherein said method of successively eluting components of a first hydrocarbon sample and then a second, different hydrocarbon sample is a method of successively eluting components of a first crude oil sample and then a second, different crude oil sample.

3. A method of successively eluting components of a first hydrocarbon sample and then a second, different hydrocarbon sample as described in claim 1 wherein said method of successively eluting components of a first hydrocarbon sample and then a second, different hydrocarbon sample is a method of successively eluting components of a first heavy oil sample and then a second, different heavy oil sample.

4. A method of successively eluting components of a first hydrocarbon sample and then a second, different hydrocarbon sample as described in claim 1 wherein said method of successively eluting components of a first hydrocarbon sample and then a second, different hydrocarbon sample is a method of successively eluting components of a first opportunity crude oil sample and then a second, different opportunity crude oil sample.

5. A method of successively eluting components of a first hydrocarbon sample and then a second, different hydrocarbon sample as described in claim 1 wherein said method of successively eluting components of a first hydrocarbon sample and then a second, different hydrocarbon sample is a method of successively eluting components of a first maltenes sample generated from a first oil and then a second, different maltenes sample generated from a second oil.

6. A method of successively eluting components of a first hydrocarbon sample and then a second, different hydrocarbon sample as described in claim 1 further comprising the steps of reversibly adsorbing highly aromatic materials of said first and second, different hydrocarbon samples.

7. A method of successively eluting components of a first hydrocarbon sample and then a second, different hydrocarbon sample as described in claim 1 further comprising the steps of analyzing said saturates, aromatics and resins components of said first and second, different hydrocarbon samples to generate analysis results.

8. A method of successively eluting components of a first hydrocarbon sample and then a second, different hydrocarbon sample as described in claim 1 further comprising the step of solvent flushing said particular bulk quantity of said non-porous, high surface energy stationary phase and said particular bulk quantity of said active stationary phase after performing said step of eluting a resins component of said first hydrocarbon sample but before performing said step of entraining said second, different hydrocarbon sample of a hydrocarbon into and as part of a second run amount of said first solvent mobile phase.

9. A method of successively eluting components of a first hydrocarbon sample and then a second, different hydrocarbon sample as described in claim 1 wherein said step of entraining said first hydrocarbon sample into and as part of a first run amount of a first solvent mobile phase comprises the step of entraining said first hydrocarbon sample into and as part of a first run amount of a mobile phase that comprises a solvent selected from the group consisting of: pentane, hexane, heptane, iso-octane, and trimethylpentane.

10. A method of successively eluting components of a first hydrocarbon sample and then a second, different hydrocarbon sample as described in claim 1 wherein said step of passing said first run amount of said first solvent mobile phase over a particular bulk quantity of a non-porous, high surface energy stationary phase comprises the step of passing said first run amount of said first solvent mobile phase over a particular bulk quantity of a stationary phase that comprises a medium selected from the group consisting of: glass, ceramics and metal.

11. A method of successively eluting components of a first hydrocarbon sample and then a second, different hydrocarbon sample as described in claim 1 wherein said step of passing said first run amount of said first solvent mobile phase over a particular bulk quantity of an active stationary phase comprises the step of passing said first run amount of said first solvent mobile phase over a particular bulk quantity of a stationary phase that comprises a medium selected from the group consisting of: activity enhanced silica and activity enhanced alumina.

12. A method of successively eluting components of a first hydrocarbon sample and then a second, different hydrocarbon sample as described in claim 1 wherein said step of passing a first run amount of a second solvent mobile phase over a particular bulk quantity of an active stationary phase comprises the step of passing a first run amount of a toluene over a particular bulk quantity of an active stationary phase.

13. A method of successively eluting components of a first hydrocarbon sample and then a second, different hydrocarbon sample as described in claim 1 wherein said step of passing a first run amount of a third solvent mobile phase over said particular bulk quantity of said non-porous, high surface energy stationary phase comprises the step of passing a first run amount of methylene chloride:methanol over said particular bulk quantity of said non-porous, high surface energy stationary phase.

14. A method of successively eluting components of a first hydrocarbon sample and then a second, different hydrocarbon sample as described in claim 1 further comprising the step of passing said first run amount of said first solvent mobile phase over a particular bulk quantity of less active stationary phase that is distinct from said particular bulk quantities of said non-porous, high surface energy stationary phase and said active stationary phase, wherein said less active stationary phase is less active than said non-porous, high surface energy stationary phase and said active stationary phase.

15. A method of successively eluting components of a first hydrocarbon sample and then a second, different hydrocarbon sample as described in claim 1 further comprising the step of passing said first run amount of said first solvent mobile phase over a particular bulk quantity of an inert stationary phase.

16. A method of successively eluting components of a first hydrocarbon sample and then a second, different hydrocarbon sample as described in claim 15 wherein said inert stationary phase comprises polytetrafluoroethylene.

17. A method of successively eluting components of a first hydrocarbon sample and then a second, different hydrocarbon sample as described in claim 15 further comprising the step of precipitating asphaltenes of said first hydrocarbon sample within said inert stationary phase.

18. A method of successively eluting components of a first hydrocarbon sample and then a second, different hydrocarbon sample as described in claim 15 further comprising the step of passing at least one asphaltene solvent over said particular bulk quantity of said inert stationary phase.

19. A method of successively eluting components of a first hydrocarbon sample and then a second, different hydrocarbon sample as described in claim 18 further comprising the step of eluting an asphaltene component of said first hydrocarbon sample.

20. A method of successively eluting components of a first hydrocarbon sample and then a second, different hydrocarbon sample as described in claim 18 further comprising the step of passing said second run amount of said first solvent mobile phase over said particular bulk quantity of an inert stationary phase.

21. A method of successively eluting components of a first hydrocarbon sample and then a second, different hydrocarbon sample as described in claim 20 further comprising the step of precipitating asphaltenes of said second, different hydrocarbon sample within said inert stationary phase.

22. A method of successively eluting components of a first hydrocarbon sample and then a second, different hydrocarbon sample as described in claim 20 further comprising the step of passing at least one asphaltene solvent over said particular bulk quantity of said inert stationary phase.

23. A method of successively eluting components of a first hydrocarbon sample and then a second, different hydrocarbon sample as described in claim 22 further comprising the step of eluting an asphaltene component of said second, different hydrocarbon sample.

24. A method of successively eluting components of a first hydrocarbon sample and then a second, different hydrocarbon sample as described in claim 15 further comprising the step of passing said second run amount of said first solvent mobile phase over said particular bulk quantity of said inert stationary phase.

25. A method of successively eluting components of a first hydrocarbon sample and then a second, different hydrocarbon sample as described in claim 7 further comprising the step of using said analysis results to improve a process selected from the group consisting of coking onset estimation, oil processing, oil fractionating, oil production, pipeline fouling mitigation, hydrotreating, distillation, vacuum distillation, atmospheric distillation, visbreaking, blending, asphalt formation, asphalt extraction, and asphaltene content of oil measurement.

26. A method of successively eluting components of a first hydrocarbon sample and then a second, different hydrocarbon sample as described in claim 7 further comprising the step of using said analysis results to further a processing related goal selected from the group consisting of: increasing distillate yield and quality; displacing high-sulfur fuel oil; boosting propylene output; mitigating fouling and corrosion; and reducing carbon footprint.

27. A method of successively eluting components of a first hydrocarbon sample and then a second, different hydrocarbon sample as described in claim 1 further comprising the step of adding at least one additional material into and as part of at least one of said first run amount of said first solvent mobile phase and said second run amount of said first solvent mobile phase, wherein said additional material is selected from the group consisting of additive and rejuvenator.

* * * * *